US007358067B2

(12) United States Patent
Vrang et al.

(10) Patent No.: US 7,358,067 B2
(45) Date of Patent: Apr. 15, 2008

(54) FERMENTATION METHOD FOR PRODUCTION OF HETEROLOGOUS GENE PRODUCTS IN LACTIC ACID BACTERIA

(75) Inventors: Astrid Vrang, Helsinge (DK); Søren Michael Madsen, Copenhagen (DK); Lars Bredmose, Copenhagen (DK); Peter Ravn, Naerum (DK); Jose Arnau, Hellerup (DK); Mads Gronvald Johnsen, Frederiksberg (DK); Anne Cathrine Steenberg, Horsholm (DK); Hans Israelsen, Allerod (DK)

(73) Assignee: Bioneer A/S, Horsholm (DK)

( * ) Notice: Subject to any disclaimer, the term of this patent is extended or adjusted under 35 U.S.C. 154(b) by 797 days.

(21) Appl. No.: 09/982,531

(22) Filed: Oct. 19, 2001

(65) Prior Publication Data

US 2002/0137140 A1   Sep. 26, 2002

Related U.S. Application Data

(63) Continuation-in-part of application No. 09/692,205, filed on Oct. 20, 2000, now abandoned.

(51) Int. Cl.
*C12P 21/00* (2006.01)
*C12N 1/21* (2006.01)
(52) U.S. Cl. ............... 435/69.8; 435/69.1; 435/252.3
(58) Field of Classification Search ............... 435/69.1, 435/252.3
See application file for complete search history.

(56) References Cited

FOREIGN PATENT DOCUMENTS

| WO | WO 94/16086 | 7/1994 |
|---|---|---|
| WO | WO 98/10079 | 3/1998 |
| WO | 01/11060 | 2/2001 |

OTHER PUBLICATIONS deVos, Curr. Opin., 2 (3), 289-295, 1999.*
van Asseldonk et al., J. Bacteriol., 175 (6), 1637-1644, 1993.*
Callewaert et al., Appl. Environ. Microbiol., 66 (2), 606-613, 2000.*
"A Method for the Regulation of Microbial Population Density During Continuous Culture at High Growth Rates", Arch. Microbiol., 107-41-47 (1976), Martin, Glenn A., et al.
"Antitermination of Characterized Transcriptional Terminators by the *Escherichia coli* rrnG Leader Region", Bjarne Albrechtsen et al., *J. Mol. Biol.* (1990) 213, 123-134.
"Nuclease B, A Possible Precursor of Nuclease A, An Extracellular Nuclease Of Staphylococcus Aureus", Austine Davis et al., *The Journal of Biological Chemistry*, vol. 252, No. 18, Sep. 25, 1977, pp. 6544-6553.
"Insertion of Transposon Tn917 derivatives into the *Lactococcus lactis* subsp. *lactis* Chromosome", Hans Israelsen et al., Applied And Environmental Microbiology, vol. 59, No. 1, Jan. 1993, p. 21-26.

"Inducible Gene Expression Systems in *Lactococcus lactis*", Djordjevic et al, *Molecular Biotechnology*, 1998, vol. 9, p. 127-139.
"Controlled Gene Expression Systems for *Lactococcus lactis* with the food-Grade Inducer Nisin", Pascalle G. G. A. De Ruyter et al., Applied And Environmental Microbiology, vol. 62, No. 10, Oct. 1996, p. 3662-3667.
"Plasmid Complements of *Streptococcus lactis* NCDO 712 and Other Lactic Streptococci After Protoplast-Induced Curing", Michael J. Gasson, *Journal of Bacteriology*, Apr. 1983, vol. 154, No. 1, p. 1-9.
"Differential plasmid rescue from transgenic mouse DNAs into *Escherichia coli* methylation-restriction mutants", Grant et al., *Proc. Natl. Acad. Sci.*, Jun. 1990, vol. 87, p. 4645-4649.
"Minimal Requirements for Exponential Growth of *Lactococcus lactis*", Peter Ruhdal Jensen et al., Applied and Environmental Microbiology, vol. 59, No. 12, Dec. 1993, p. 4363-4366.
"Bioenergetics of lactic acid bateria: cytoplasmic pH and osmotolerance", Eva R. Kashket, FEMS Microbiology Reviews 46 (1987) 233-244.
"High-Frequency Transformation, by Electroporation, of *Lactococcus lactis* subsp. *cremoris* Grown with Glycine in Osmotically Stabilized Media", Holo et al., *Applied and Environmental Microbiology*, Dec. 1989, vol. 55, No. 12, p. 3119-3123.
"Controlled overproduction of proteins by lactic acid bacteria", Oscar P. Kuipers et al., TIB Tech, vol. 15, Apr. 1997.
"Heterologous protein secretion in *Lactococcus lactis*: a novel antigen delivery system", P. Langella et al., Brazilian Journal of Medical and Biological Research (1999) 32:191-198.
"Direct Screening of Recombinants in Gram-Positive Bacteria Using the Secreted Staphylococcal Nuclease as a Reporter", Y. Le Loir et al., Journal of Bacteriology, Aug. 1994, vol. 176, No. 16, p. 5135-5139.
"A Nine-Residue Synthetic Propeptide Enhances Secretion Efficiency of Heterologous Proteins in *Lactococcus lactis*", Y. Le Loire et al., Journal of Bacteriology, Apr. 1998, vol. 180, No. 7, p. 1895-1903.
"Influence of end-products inhibition and nutrient limitations on the growth of *Lactococcus lactis*subsp. *lactis*", Journal of Applied Microbiology, 1997, 82-95-100.
"Design of thermolabile bacteriophage repressor mutants by comparative molecular modeling", Arjen Nauta et al., Nature Biotechnology, Oct. 1997, vol. 15.

(Continued)

*Primary Examiner*—Nancy T. Vogel
(74) *Attorney, Agent, or Firm*—Roberts, Mlotkowski & Hobbes P.C.

(57) ABSTRACT

The invention provides a fed-batch or continuous process for producing heterologous peptides, polypeptides or proteins in lactic acid bacteria, comprising the steps of (i) constructing a recombinant lactic acid bacterium comprising a nucleotide sequence coding for the heterologous peptide, polypeptide or protein, and appropriate regulatory nucleotide sequences such as regulatable promoters and signal peptides to control the expression of the coding sequence and the secretion of gene product, (ii) cultivating the recombinant bacterium under or continuous cultivation conditions to express the gene, and (iii) harvesting the recombinant bacterium or the gene product. Preferably, the cultivation medium is a chemically defined or synthetic medium optionally supplemented with yeast extract.

31 Claims, 22 Drawing Sheets

OTHER PUBLICATIONS

"High- and low-copy-number *Lactococcus* shuttle cloning vectors with features for clone screening", Daniel J. O'Sullivan et al., GENE 07541, 1993, 227-231.

"An Export-Specific Reporter Designed for Gram-Positive Bacteria: Application to *Lactococcus lactis*", Isabelle Poquet et Journal of Bacteriology, Apr. 1998, vol. 180, No. 7, p. 1904-1912.

"Cloning and Partial Characterization of Regulated Promoters from *Lactococcus lactis* TN*917-lacZ* Integrants with the New Promoter Probe Vector, pAK80" by Israelsen et al., Jul. 1995, *Applied and Environmental Microbiology*, vol. 61, No. 7, p. 2540-2547.

"Inducible gene expression and environmentally regulated genes in lactic acid bacteria", *Antonie van Leeuwenoek*, Kok et al, 1996, 70, p. 129-145.

"Molecular characterization of the pH-inducible and growth phase-dependent promoter P170 of *Lactococcus lactis*", Madsen et al., *Molecular Microbiology*, 1999, 32(1), p. 75-87.

"Rapid Mini-Prep Isolation of High-Quality Plasmid DNA from *Lactococcus* and *Lactobacillus* spp.", O'Sullivan et al., *Applied and Environmental Microbiology*, Aug. 1993, vol. 59, No. 8, p. 2730-2733.

"Molecular Characterization of a Phage-Inducible Middle Promoter and Its Transcriptional Activator from the Lactococcal Bacteriophage ø31", Walker et al., *Journal of Bacteriology*, Feb. 1998, vol. 180, No. 4, p. 921-931.

"Development of an Expression Strategy Using a Lytic Phage to Trigger Explosive Plasmid Amplification and Gene Expression", Daniel J. O'Sullivan et al., Biotechnology, vol. 14, Jan. 1996.

"The development of Tn*Nuc* and its use for the isolation of novel secretion signals in *Lactococcus lactis*", Peter Van et al., GENE 242 (2000) 347-356.

"Identification of a sodium chloride-regulated promoter in *Lactococcus lactis* by single-copy chromosomal fusion with a reporter gene", J. W. Sanders et al., Mol Gen Genet (1998) 257:681-685.

"Cloning of usp45, a gene encoding a secreted protein from *Lactococcus lactis* subsp. *lactis* MG1363", Martien van Asseldonk, et al., GENE 03731, 1990, pp. 155-159.

"Cloning, Nucleotide Sequence, and Regulatory Analysis of the *Lactococcus lactis dna*J Gene", Martien van Aseldonk et al., Journal of Bacteriology, Mar. 1993, vol. 175, No. 6, p. 1637-1644.

"Isolation and Characterization of *Streptococcus cremoris* Wg2-Specific Promoters", Applied and Environmental Microbiology, Oct. 1987, vol. 53, No. 10, p. 2452-2457.

European International Search Report dated Aug. 14, 2002 for Application No. PCT/DK01/00693, Filed Oct. 19, 2001.

Marléne Imbert et al., On the Iron Requirement of *Lactobacilli* Grown in Chemically Defined Medium, *Current Microbiology*, Jul. 1998; 37(1):64-66.

M. Elli et al., Iron Requirement Of *Lactobacillus* spp. in Completely Chemically Defined Growth Media, *Journal of Applied Microbiology*, Apr. 2000; 88(4): 695-703.

Sandrine Petry et al., Factors Affecting Exocellular Polysaccharide Production by *Lactobacillus delbrueckii* subsp. *bulgaricus* Grown in a Chemically Defined Medium., *Applied Environmental Microbiology*, Aug. 2000; 66(8):3427-3431.

Erwin Glaasker et al., Osmotic Regulation of Intracellular Solute Pools in *Lactobacillus* plantarum, *Journal of Bacteriology*, Feb. 1996; 178(3):575-82.

Walter A. Zygmunt; Reversal of d-Cycloserine Inhibition of Bacterial Growth by Alanine, *Journal of Bacteriology*, Jul. 1962; 84(1):154-156.

\* cited by examiner

| Strain | Plasmid | Copy-number | Construction | | | SNase, u/m | |
| --- | --- | --- | --- | --- | --- | --- | --- |
| SMBI no. | pSMBI no. | | Promoter | SP | Coding Sequence | Flask | Fermer |
| 111 | 109 | Medium | P170 | 310mut2 | Nuc | 0.88 | 3.1 |
| 105 | 93 | Medium | P170 | Usp45 | Nuc | 1.04 | 3.4 |
| 104 | 91 | High | P170 | 310mut2 | Nuc | 2.25 | 8.7 |
| 106 | 98 | High | P170 | Usp45 | Nuc | 2.77 | 10.2 |

Fig. 1

FERMENTATION METHOD FOR PRODUCTION OF HETEROLOGOUS GENE PRODUCTS IN LACTIC ACID BACTERIA

This application is a continuation in part of U.S. patent application Ser. No. 09/692,205 filed Oct. 20, 2000, entitled "Improved Method for Production of Heterologous Gene Products in Lactic Acid Bacteria.", now abandoned, the contents of which are incorporated herein in their entirety to the extent that it is consistent with this invention and application.

FIELD OF INVENTION

The present invention relates in its broadest aspect to the field of producing recombinant bacterial cells, peptides, polypeptides or proteins using recombinant DNA technology and in particular to the use of gene expression systems in a lactic acid bacterial host cell. Specifically, the invention provides a fed-batch or continuous fermentation process using such gene expression systems permitting effective production in lactic acid bacteria of heterologous peptides, polypeptides or proteins including enzymes and pharmaceutically active products.

PRIOR ART AND TECHNICAL BACKGROUND

A number of considerations must be made in order to select a suitable system for over-expression of a desired gene product. Important issues include the yield of heterologous gene product required, costs of using the expression system and the authenticity/biological activity of the recombinant gene product produced in the production host.

As high-level production of a heterologous peptides, polypeptides or proteins will be a burden to the host cell, it may be advantageous to use an inducible, i.e. regulatable gene expression system that can be repressed during propagation of the production organism, both to avoid prolonged cultivation periods and to minimise the risk of selecting non-producing variants.

To develop an inducible expression system, which is suitable for production on an industrial scale, it is also important that induction of the system does not imply technical difficulties or the use of costly or toxic substances. Besides the quantity of product obtained from the production organism, the purity of the produced gene product is very important. A high yield of product contained in a whole-cell lysate may be reduced substantially during the subsequent steps of down-stream processing required to remove undesired host cell components. Therefore, secretion to either the periplasm in gram-negative bacteria or to the extracellular environment of gram-positive bacteria is generally preferred.

Until now *Escherichia coli* and *Bacillus subtilis* have been the most widely used bacterial host organisms for the recombinant production of peptides, polypeptides and proteins. The molecular biology of these organisms is characterised to a level that exceeds that for all other prokaryotic microorganisms and this extensive research has formed the basis for generating a large collection of genetic tools that have enabled easy cloning and expression of heterologous genes in these bacteria.

However, during the last decade there has been an increasing focus on the development of lactic acid bacteria (LAB) and in particular *Lactococcus lactis* as cell factories for production of homologous or heterologous peptides, polypeptides and proteins. LAB are advantageous for production of heterologous gene products in several aspects. The production and administration of recombinant peptides, polypeptides and proteins for pharmaceutical applications are subject to strict demands by regulatory authorities worldwide. For example, endotoxins, a component of the cell wall in most gram-negative bacteria, should be absent in the final product. Lactic acid bacteria do not produce endotoxins, which makes them attractive protein production host organisms. In addition, several lactic acid bacterial strains including *L. lactis* strains do not produce extracellular proteases and are capable of secreting peptides, polypeptides or proteins ensuring high gene product stability facilitating the subsequent purification hereof.

The design of a number of promising inducible gene expression systems for use in lactic acid bacteria (Kok, 1996; Kuipers et al., 1997; Djordjevic and Klaenhammer, 1998) has been achieved through studies focusing on the regulation of gene expression in *L. lactis* and their phages. Useful lactic acid bacterial expression systems include the NICE system (de Ruyter et al., 1996), which is based on genetic elements from a two-component system that controls the biosynthesis of the anti-microbial peptide nisin in *L. lactis*. Two other useful inducible expression systems are based on genetic elements from the *L. lactis* bacteriophages φ31 (O'Sullivan et al., 1996; Walker and Klaenhammer, 1998) and r1t (Nauta et al., 1997).

Promoterless reporter genes in transposons, integration vectors or plasmids (van der Vossen et al., 1987; Israelsen and Hansen, 1993; Sanders et al., 1998) have been used to identify inducible promoters in LAB. These promoters are induced by changes in the environment such as pH (Israelsen et al., 1995) and concentration of salt (Sanders et al., 1998).

Gene expression systems induced by metabolites produced by the host cell or by conditions naturally occurring during host cell growth are of industrial interest due to the low cost and food grade status of the inducing factor. Therefore, we have exploited inducible promoters including the pH inducible P170 and derivatives hereof as disclosed in the co-owned published international patent applications WO 94/16086 and WO 98/10079 in the development of a new gene expression system for use in *L. lactis*. The transcription from the P170 promoter is induced by low pH during the concomitant transition to stationary phase, ie the expression is repressed during exponential growth phase. In a recent study, the P170 promoter was characterised in detail and the original expression level was increased approximately 150-200 fold by genetic engineering, without affecting the regulation (Madsen et al., 1999).

Although attempts to achieve cost-effective levels of gene product using lactic acid bacterial host cells have been promising, there is, however, a continued industrial need to increase the productivity of such production systems. Additionally, there is a need to provide fermentation processes where the medium does not contain potentially hazardous components that can be a health risk to the end-user of the products. Examples of such undesired components include animal viruses and prions, the presence of which cannot be completely excluded in conventional fermentation media containing components of animal origin such as nitrogenous components. However, most presently used fermentation media are chemically undefined media containing such components of animal origin.

There is therefore a strong demand to provide methods for producing heterologous peptides, polypeptides or proteins which methods are absolutely safe and which permit the desired gene products to be provided at the same and preferably higher yields than do current production methods.

Current methods of producing heterologous gene products using lactic acid bacterial host cells are based on batch cultivation of the host cells in chemically undefined, nutrient rich media. The present invention encompasses the use of a chemically defined, ie synthetic medium is such production processes. It was found that the use of such media in a conventional batch process resulted in a yield of gene product that was significantly lower than that achieved in a conventional nutrient rich and chemically undefined medium. It was, however, found that this problem could be overcome by performing the production process as a continuous process or a fed-batch process.

SUMMARY OF THE INVENTION

Accordingly, the present invention provides in its broadest aspect a method of producing a heterologous peptide, polypeptide or protein in a lactic acid bacterium, the method comprising the steps of
(i) constructing a recombinant lactic acid bacterium comprising a nucleotide sequence coding for the heterologous peptide, polypeptide or protein and operably linked thereto, appropriate regulatory nucleotide sequences to control the expression of the coding sequence,
(ii) cultivating said recombinant bacterium under fed-batch or continuous cultivation conditions to express the gene, and
(iii) harvesting the recombinant bacterium, the peptide, polypeptide or protein.

Appropriate regulatory nucleotide sequences include constitutive promoters or regulatable, ie inducible, promoters. In embodiments where a regulatable promoter is used, such a promoter is preferably regulated by an environmental factor present during cultivation of the recombinant bacterium implying that it is not required to add inducing substances to the medium. Particularly useful regulatable promoters include the lactic acid bacterial pH regulatable promoter P170 and derivatives hereof as disclosed in WO 94/16086 and WO 98/10079.

In a further aspect the invention pertains to a chemically defined basal medium (LM1 medium) for cultivating lactic bacteria, the medium consisting of:

| Component | Concentration, mM or +/− |
|---|---|
| L-Alanine | 3.4 |
| L-Arginine | 1.1 |
| L-Asparagine | 0.8 |
| L-Cysteine | 0.8 |
| L-Glutamate | 2.1 |
| L-Glutamine | 0.7 |
| Glycine | 2.7 |
| L-Histidine | 0.3 |
| L-Isoleucine | 0.8 |
| L-Leucine | 0.8 |
| L-Lysine-HCl | 1.4 |
| L-Methionine | 0.7 |
| L-Phenylalanine | 1.2 |
| L-Proline | 2.6 |
| L-Serine | 2.9 |
| L-Threonine | 1.7 |
| L-Tryptophan | 0.5 |
| L-Tyrosine | 0.3 |
| L-Valine | 0.9 |
| $K_2SO_4$ | 0.28[a] |
| $KH_2PO_4/K_2HPO_4$ | 4/6 |
| Na-acetate | 15 |

-continued

| Component | Concentration, mM or +/− |
|---|---|
| $CaCl_2$ | 0.0005[a] |
| $MgCl_2$ | 0.52a |
| $FeSO_4$ | 0.01[a] |
| Vitamins[b] | + |
| Micronutrients[a,c] | + |
| Citric acid | 0.1 |

[a]From Neidhardt et al. J. Bacteriol. 119: 736-747
[b]Vitamins: 0.4 µM biotin, 10 µM pyridoxal-HCl, 2.3 µM folic acid, 2.6 µM riboflavin, 8 µM niacinamide, 3 µM thiamine-HCl and 2 µM pantothenate
[c]Micronutrients: 0.003 µM $(NH_4)_6(MO_7)_{24}$, 0.4 µM $H_3BO_4$, 0.03 µM $CoCl_2$, 0.01 µM $CuSO_4$, 0.08 µM $MnCl_2$ and 0.01 µM $ZnSO_4$.

In still further aspects the invention relates to a chemically defined medium (LM3 medium) for cultivating lactic acid bacteria containing all the components of the LM1 medium in three-fold amounts, except the phosphates and sodium acetate, the respective amounts of which are kept at the same level as in the LM1 medium, and a chemically defined medium (LM5 medium) for cultivating lactic acid bacteria containing all the components of the LM1 medium in five-fold amounts, except the phosphates and sodium acetate, the respective amounts of which are kept at the same level as in the LM1 medium.

DETAILED DISCLOSURE OF THE INVENTION

One primary objective of the present invention is to provide improved methods of producing recombinant lactic acid bacteria and producing heterologous peptides, polypeptides or proteins in a lactic acid bacterium.

As used herein the term "lactic acid bacterium" designates a gram-positive, microaerophilic or anaerobic bacterium which ferments sugars with the production of acids including lactic acid as the predominantly produced acid. The industrially most useful lactic acid bacteria are found among *Lactococcus* spp., *Streptococcus* spp., *Lactobacillus* spp., *Leuconostoc* spp., *Pediococcus* spp., *Brevibacterium* spp. and *Propionibacterium* spp. Additionally, lactic acid producing bacteria belonging to the group of the strictly anaerobic bacteria, bifidobacteria, ie *Bifidobacterium* spp., which are frequently used as food starter cultures alone or in combination with lactic acid bacteria, are generally included in the group of lactic acid bacteria.

In a first step of the present method, a recombinant lactic acid bacterium is constructed to comprise a nucleotide sequence that codes for the desired heterologous peptide, polypeptide or protein and operably linked thereto, appropriate regulatory nucleotide sequences to control the expression of the coding sequence. Such a construction can be made using methods that are well-known in the art, e.g. using the methods described in Sambrook et al., 1989.

In useful embodiments the nucleotide sequence coding for a desired gene product is selected from a sequence coding for an enzyme including a lipase, a peptidase, a protease including an aspartic protease having milk clotting activity such as chymosin, pepsin and aspartic proteases of microbial origin, a nuclease, an enzyme involved in carbohydrate metabolism including amylases and other starch degrading enzymes, oxidoreductases including as examples glucose oxidase and hexose oxidase, and a lytic enzyme, a nucleotide sequence coding for a viral protein such as a capsid protein, a sequence coding for a microbial cell surface protein structure and a sequence coding for a bacteriocin such as e.g. nisin, reuterin and pediocin. The nucleotide sequence may also be one which codes for a gene product conferring resistance to an antibiotic.

In particularly interesting embodiments, the recombinant lactic acid bacterium comprises a nucleotide sequence coding for a biologically functional gene product including a microbial toxin, an immunologically active peptide or polypeptide, a pharmaceutically active peptide, polypeptide or protein, and an antimicrobially active peptide, polypeptide or protein.

In the present context, immunologically active gene products include any amino acid sequences which comprise at least one epitope. Such sequences are useful as vaccines and/or diagnostic agents, and can be derived from any pathogenic organism against which there is a need to immunise an animal such as a mammal including a human being. It will be understood that the epitope expressed by the coding nucleotide sequence can be one which is secreted out of the cell into the culture medium or it can be located on the outer surface of the host organism whereby it will be possible to apply the recombinant cell itself as a vaccine. Alternatively, the epitope can be produced intracellularly, in which case it is isolated from the cell. Another interesting means of having an epitope expressed is by inserting the nucleotide sequence coding for the epitope into a further coding sequence such that the epitope in an immunologically active form is expressed as part of a fusion protein.

In a specific embodiment, the coding nucleotide sequence codes for a mycobacterial antigenic determinant or epitope, ie an immunologically active oligo- or polypeptide which, when administered to an animal including a human being, has a stimulating effect on the humoral and/or cellular immune response. In particular, such a coding sequence may be derived from an organism that belongs to the group of Mycobacterium species which is generally referred to as the "tuberculosis complex" that includes *Mycobacterium tuberculosis, M. bovis* and *M. africanum*. Such antigenic gene products of mycobacterial origin have potential use as tuberculosis vaccines and/or as diagnostic reagents in the tuberculosis skin test. It is evident that industrial production of vaccines and diagnostically active agents for human and animal use in a safe, non-pathogenic organism as a lactic acid bacterium will be highly advantageous.

In further useful embodiments, the coding nucleotide sequence is one that codes for an antibody including a monoclonal and a polyclonal antibody. Such a coding sequence can be derived from any animal source including birds, mammals and human beings.

In accordance with the method of the invention the recombinant cell may comprise at least one constitutive promoter or at least one regulatable promoter operably linked to the coding nucleotide sequence, the term "promoter" being used in the conventional sense to designate a site whereto RNA polymerase can be bound.

The promoter region may, in accordance with the invention be derived from any prokaryotic cell, but in preferred embodiments it is derived from a lactic acid bacterial species including the above species and Bifidobacterium spp. In useful embodiments, the promoter region is derived from a promoter region of *Lactococcus lactis* including *Lactococcus lactis* subspecies *lactis*, e.g. the strain designated MG1363 [this strain is also referred to in the literature as *Lactococcus lactis* subspecies *cremoris* (Nauta et al., 1996)], and *Lactococcus lactis* subspecies *lactis* biovar. *diacetylactis*. Examples of such promoter regions which, in accordance with the present invention, are useful in the construction of the recombinant lactic acid bacterium are given in WO 94/16086, including a region comprising the promoter P170, and derivatives hereof, examples of which are disclosed in WO 98/10079.

As it is mentioned above, it may for certain purposes be advantageous that the promoter used in the recombinant lactic acid bacterium is a regulatable or inducible promoter. The factor(s) regulating or inducing the promoter include any physical and chemical factor that can regulate the activity of a promoter sequence, including physical conditions such as temperature and light, chemical substances such as e.g. IPTG, tryptophan, lactate or nisin. In presently preferred embodiments a regulatable promoter used in the invention is regulated by an environmental or growth condition factor that occurs during the cultivation step. The advantages of using such a regulatable promoter is that there is no need to add inducing or regulating compounds to the cultivation medium. Such a regulating factor is selected from pH, the growth temperature, the oxygen content, a temperature shift eliciting the expression of heat chock genes, the composition of the growth medium including the ionic strength/NaCl content, accumulation intracelllularly or in the medium of metabolites including lactic acid/lactate, the presence/absence of essential cell constituents or precursors herefor, the growth phase of the bacterium or the growth rate of the bacterium.

It will be understood that when the promoter is one, the induction or regulation of which is controlled by one or more substances present in a growth medium, substances which are not normally components of such media, such as antibiotics or bacteriocins are, in accordance with the invention, generally not included as environmental or growth condition factors.

In one preferred embodiment, the promoter and the nucleotide coding for the heterologous peptide, polypeptide or protein is introduced into the lactic acid bacterium on an autonomously replicating replicon such as a plasmid, a transposable element, a bacteriophage or a cosmid. It may be advantageous to introduce the promoter and the coding sequence under conditions where at least the coding sequence becomes integrated into the host cell chromosome, as this provides stable maintenance in the cell of the coding sequence. Alternatively, the heterologous coding sequence is introduced into the host cell chromosome at a location where it becomes operably linked to a promoter naturally occurring in the chromosome of the selected host organism. Thus, in a further embodiment, the promoter that is operably linked to the nucleotide sequence coding for the heterologous peptide, polypeptide or protein is a promoter not naturally associated with said coding sequence.

In a further advantageous embodiment the coding nucleotide sequence is operably linked to a nucleotide sequence coding for a signal peptide (SP) permitting that the gene product is secreted over the cell membrane and into the medium. SPs are the N-terminal extensions present in Sec-dependent secreted proteins. The structure of a typical SP includes three distinct regions: (i) an N-terminal region that contains a number of positively charged amino acids, lysine and arginine; (ii) a central hydrophobic core and; (iii) a hydrophilic C-terminus that contains the sequence motif recognised by the signal peptidase. Proteins that are targeted for secretion include a signal sequence or signal peptide (SP) at the N-terminus. SPs are recognised and cleaved by a leader or signal peptidase, a component of the secretion machinery of the cell, during translocation across the cell membrane. SPs are normally 25 to over 35 amino acids (aa) in size in gram-positive bacteria. SPs do not share sequence homology, but are often composed of an amino terminus that includes one or more basic aa, a central hydrophobic core of seven or more aa, and a hydrophilic carboxy terminus containing the motif that is recognised by signal peptidases. A survey of available SPs from L. lactis suggested the use of the SP from Usp45, the major secreted lactococcal protein (van Asseldonk et al., 1990). This SP was reported to be functional in the secretion of several heterologous proteins in L. lactis (van Asseldonk et al., 1993).

In a specific embodiment, the signal peptide is selected from the group consisting of the Usp45 signal peptide and the signal peptide having the sequence (SEQ ID NO: 1)
MKFNKKRVAIATFIALIFVSFFTISSQDAQAAERS.

In a subsequent step of the method according to the invention, the thus obtained recombinant lactic acid bacterium is cultivated under or continuous cultivation conditions to express the sequence coding for the desired gene product and the recombinant cells or the peptide, polypeptide or protein is harvested, either during the cultivation (when continuous) or when the cultivation step is terminated (when) using conventional techniques for separating cells, peptides, polypeptides and proteins.

In the broadest sense the expression "cultivation" is defined as a cultivation technique where one or more nutrients are supplied during cultivation to the cultivation container or bioreactor and in which the cultivated cells and the gene product remain in the containment until the end of the run. In some cases, all nutrients are gradually fed to the bioreactor. As used herein the expression "continuous cultivation" is used to describe a cultivation process where all nutrients are continuously added to the cultivation container or bioreactor and fractions of the medium and/or cell culture are removed at the same flow rate as that of supplied nutrients to maintain a constant culture volume.

In contrast to these cultivation methods of the invention, a conventional "batch" cultivation is a process where all nutrients required during one run of cultivation, except for molecular oxygen in an aerobic process and chemicals for pH adjustment, are added to the medium before cultivation is started.

The time-temperature conditions, pH conditions and aeration conditions, if relevant, and the rate of feeding nutrients to the bioreactor will depend i.a. on the particular type of lactic acid bacterium that is used. Specific examples of such conditions are provided in the following examples. Typically, a cultivation under the above conditions is run for 24-72 hours at a temperature in the range of 15-40° C. and at a pH in the range of 4-8. A continuous cultivation process according to the invention may run, under these temperature and pH condition for longer periods of time, such as several hundred hours.

In presently preferred embodiments of the method, the recombinant lactic acid bacterium is cultivated in a chemically defined medium. As used herein the expression "chemically defined medium" denotes a medium that essentially does not contain undefined nitrogen or carbon sources such as animal or plant protein or protein hydrolysate compositions or complex carbon sources such as e.g. molasses or corn steep liquor, but wherein the nitrogen sources are well-defined inorganic or organic compounds such as ammonia or amino acids and the carbon source is a well-defined sugar such as glucose. Additionally, such a synthetic medium contains mineral components such as salts, e.g. sulfates, acetates, phosphates and chlorides of alkaline and earth alkaline metals, vitamins and micronutrients. Examples of chemically defined media for the purpose of the present invention are given herein. It will be appreciated that these media are only examples. The person of skill in the art will be able to provide other media which permit cultivation of recombinant lactic acid bacteria under the above cultivation conditions.

The synthetic medium used in the present method must contain a carbon source. The concentration of carbon source depends on the type of recombinant lactic acid bacterium and the selected cultivation conditions. In useful embodiments the carbon source is glucose. In preferred embodiments, the concentration of glucose in the culture is kept at a pre-selected concentration of at least about 0.5 g/L by controlled feeding of glucose in a process or by feeding of complete glucose-containing complete medium in a continuous cultivation process. The glucose concentration in the cultivation medium may preferably be at least 5 g/L such as at least 10, 15, 20, 30, 40, 50, 80 or 100 g/L.

In accordance with the invention, one convenient manner of controlling the feeding of glucose to the medium in a process is to link or connect such feeding to the pH control means of the bioreactor. In this manner, feeding of glucose is activated by the means controlling the automatic addition of base to control the pH. Similarly, in a continuous cultivation process, the feeding of complete medium can be linked to pH control in accordance with the pH auxostat principle.

Although it was found that satisfactory yields of gene product could be obtained by using a purely synthetic medium, it was found that the yield may be further increased by supplementing a chemically defined medium as defined above with yeast extract. A suitable amount of yeast extract is an amount in the range of 0.1-10 g/L such as e.g. in the range of 1-5 g/L. Accordingly, in the present context, a "chemically defined medium" may include a chemically defined medium enriched with an appropriate amount of yeast extract.

The main objective of the present invention is to provide a method for producing a gene product at a high yield. Accordingly, in preferred embodiments, the yield of peptide, polypeptide or protein is at least 5 mg/L, more preferably at least 10 mg/L such as at least 20 mg/L including at least 50 mg/L. In particularly preferred embodiments, the yield that is obtained is at least 100 mg/L, including at least 150 mg/L and at least 200 mg/L.

As it mentioned above, the invention relates is in further aspect to a specific chemically defined basal medium (LM1 medium) for cultivating bacteria, the medium consisting of:

| Component | Concentration, mM or +/− |
| --- | --- |
| L-Alanine | 3.4 |
| L-Arginine | 1.1 |
| L-Asparagine | 0.8 |
| L-Cysteine | 0.8 |
| L-Glutamate | 2.1 |
| L-Glutamine | 0.7 |
| Glycine | 2.7 |
| L-Histidine | 0.3 |

-continued

| Component | Concentration, mM or +/− |
|---|---|
| L-Isoleucine | 0.8 |
| L-Leucine | 0.8 |
| L-Lysine-HCl | 1.4 |
| L-Methionine | 0.7 |
| L-Phenylalanine | 1.2 |
| L-Proline | 2.6 |
| L-Serine | 2.9 |
| L-Threonine | 1.7 |
| L-Tryptophan | 0.5 |
| L-Tyrosine | 0.3 |
| L-Valine | 0.9 |
| $K_2SO_4$ | 0.28[a] |
| $KH_2PO_4/K_2HPO_4$ | 4/6 |
| Na-acetate | 15 |
| $CaCl_2$ | 0.0005[a] |
| $MgCl_2$ | 0.52[a] |
| $FeSO_4$ | 0.01[a] |
| Vitamins[b] | + |
| Micronutrients[a,c] | + |
| Citric acid | 0.1 |

[a]From Neidhardt et al. J. Bacteriol. 119: 736-747
[b]Vitamins: 0.4 μM biotin, 10 μM pyridoxal-HCl, 2.3 μM folic acid, 2.6 μM riboflavin, 8 μM niacinamide, 3 μM thiamine-HCl and 2 μM pantothenate
[c]Micronutrients: 0.003 μM $(NH_4)_6(MO_7)_{24}$, 0.4 μM $H_3BO_4$, 0.03 μM $CoCl_2$, 0.01 μM $CuSO_4$, 0.08 μM $MnCl_2$ and 0.01 μM $ZnSO_4$ There are also provided chemically defined media derived from the LM1 medium including the LM3 medium that contains all the components of the LM1 medium in three-fold amounts, except phosphates and sodium acetate, the respective amounts of which are kept at the same level as in the LM1 medium and the medium referred to as the LM5 medium that contains all of the components of the LM1 medium in five-fold amounts, except phosphates and sodium acetate, the respective amounts of which is kept at the same level as in the LM1 medium.

As also stated above, the chemically defined medium of the invention must be supplemented with a suitable defined carbon source. Accordingly, in useful embodiments, any of the above media is supplemented with glucose, typically in an amount in the range of 1-100 g/L including the range of 2-50 g/L such as in the range of 5-40 g/L.

The invention will now be described in further details in the following examples and the drawings wherein:

FIG. 1 is a schematic presentation of SNase expressing plasmids used herein. The yield of secreted SNase (units/ml) obtained in GM17 medium in flask cultures or fermentors is indicated to the right;

Figure 4A:
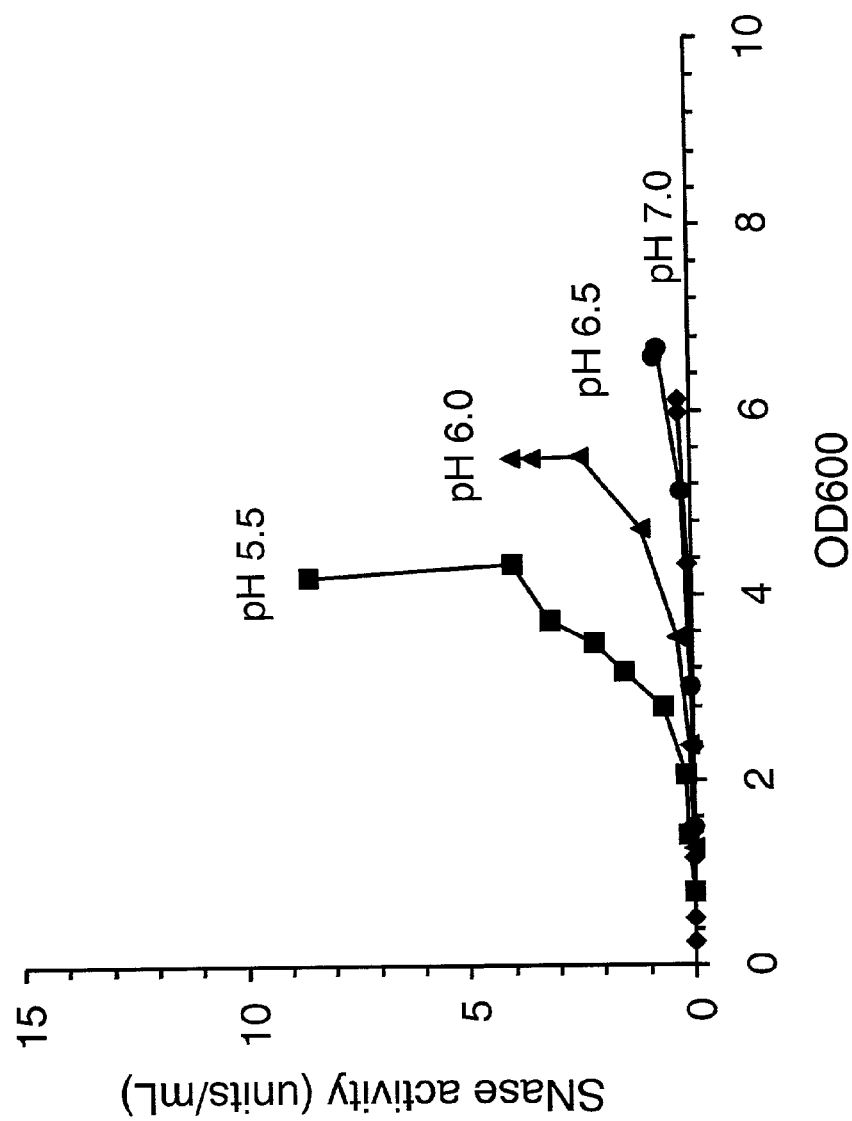
Figure 4B:
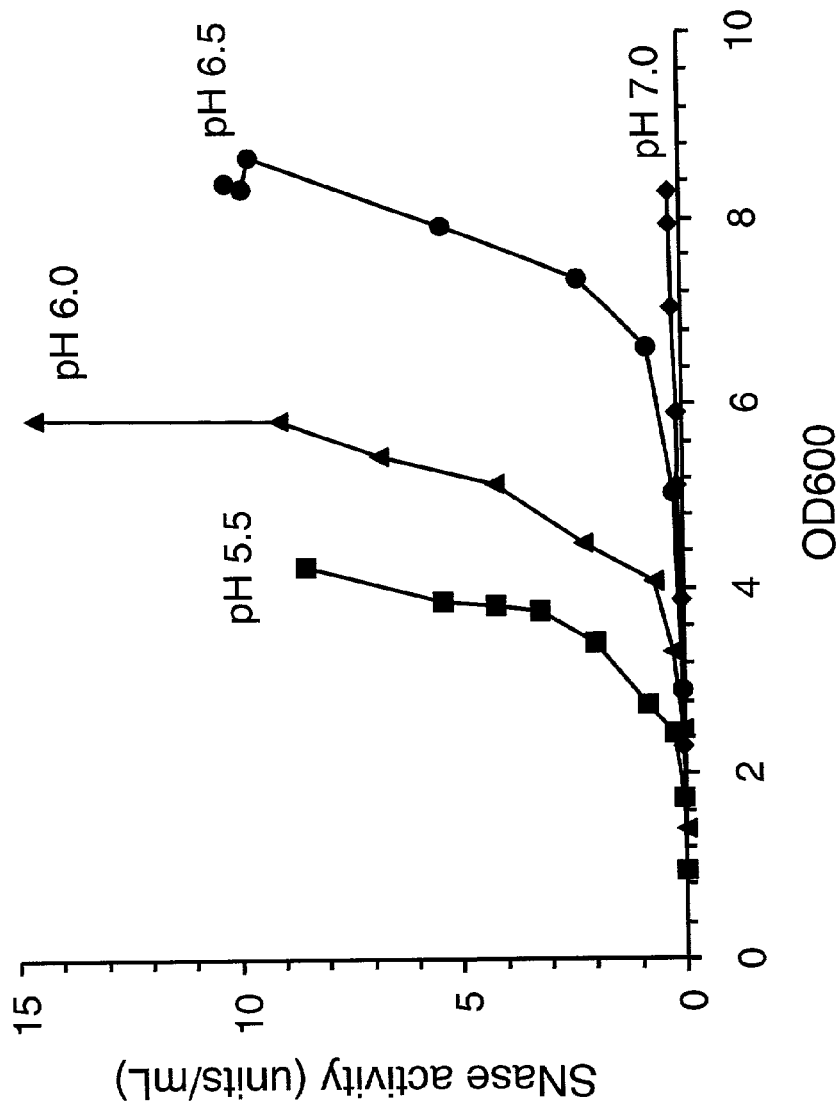
Figure 5:
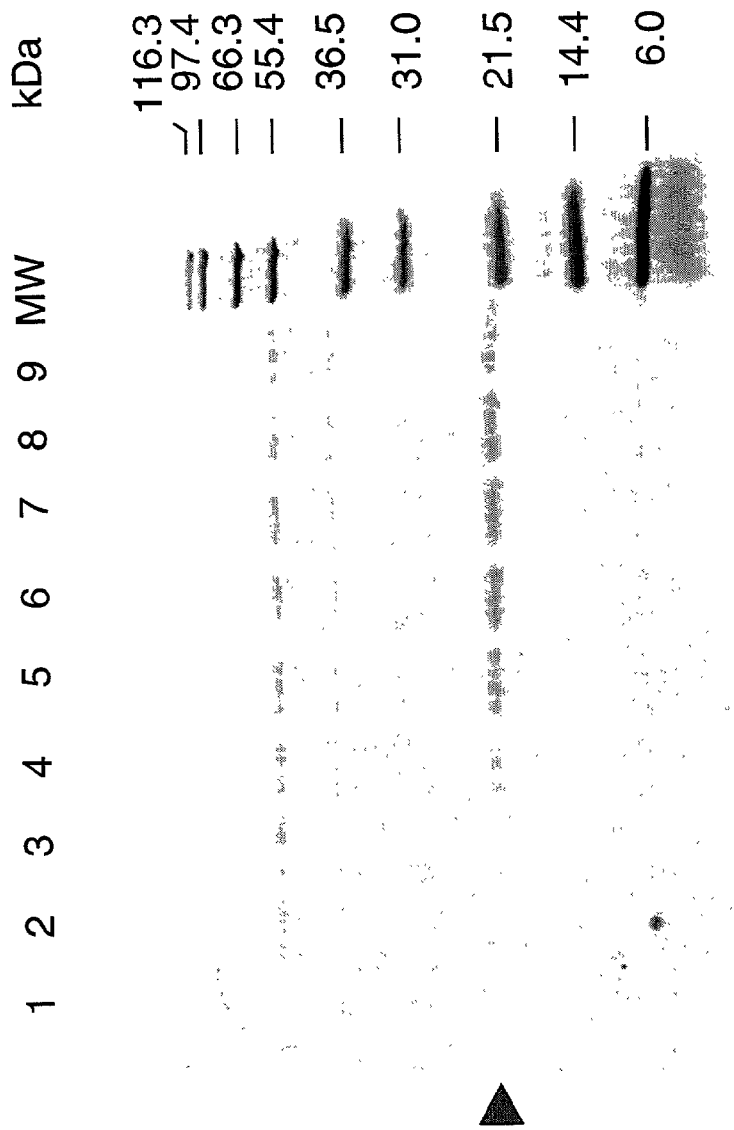
Figure 6A:
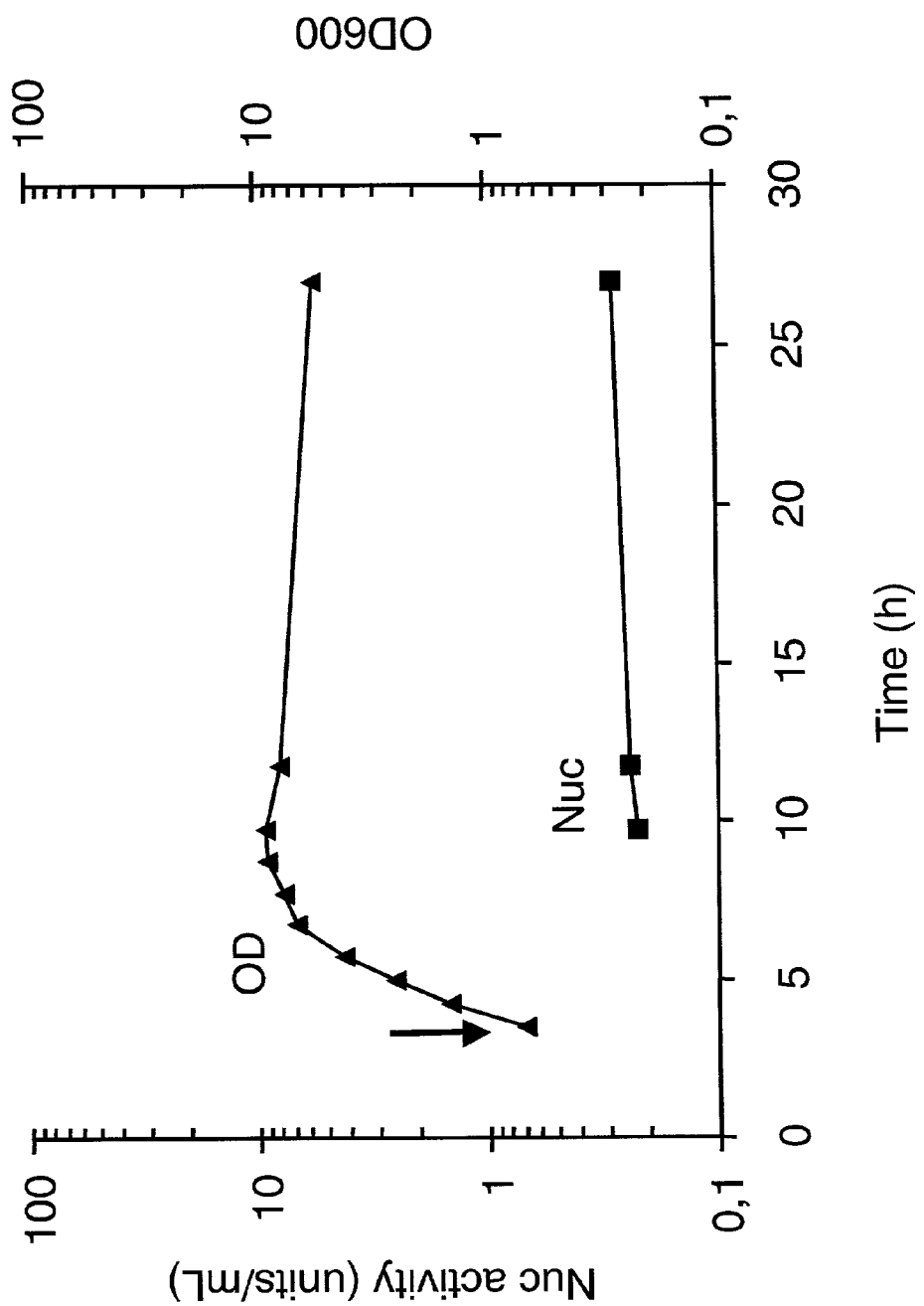
Figure 6B:
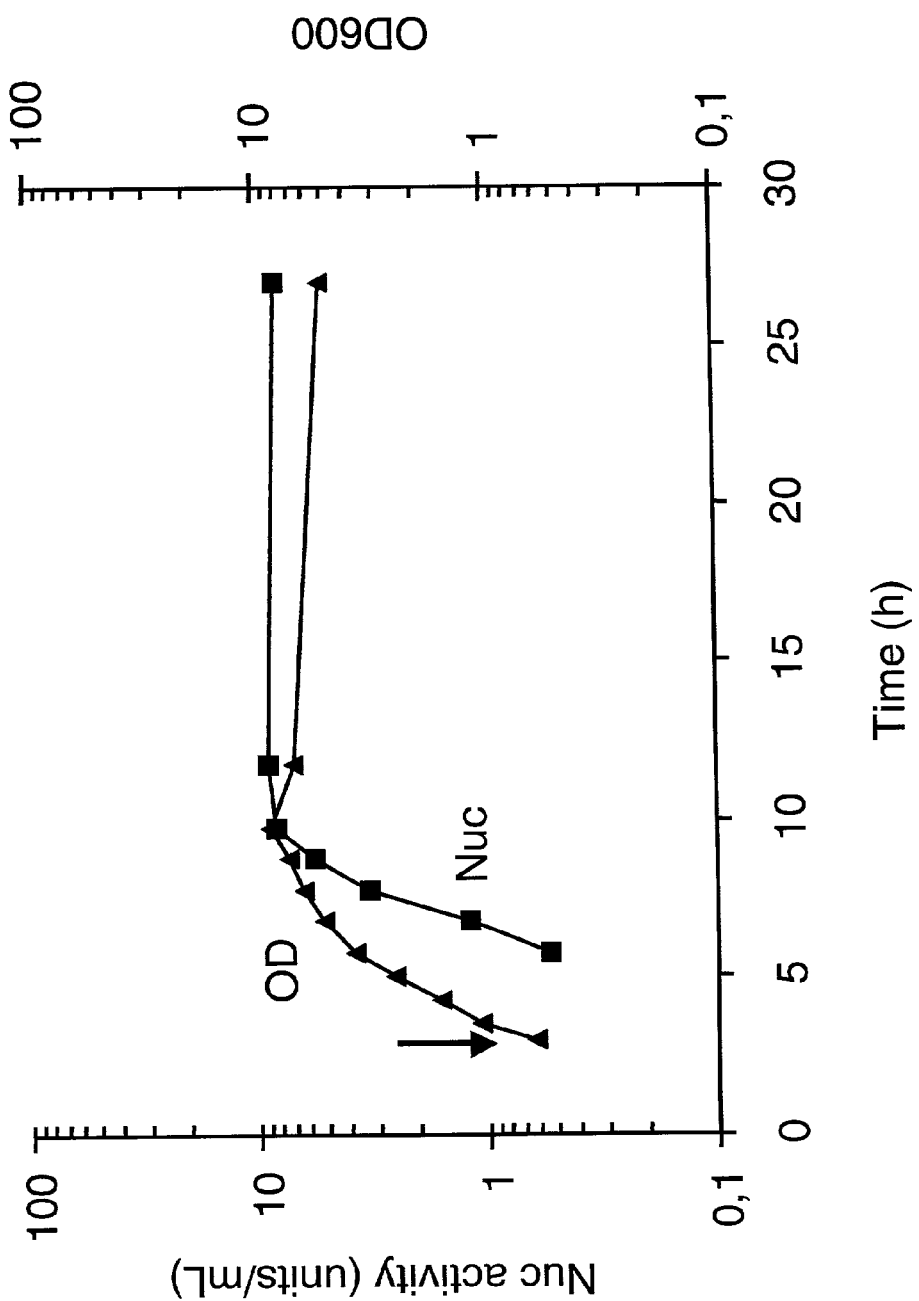
Figure 6C:
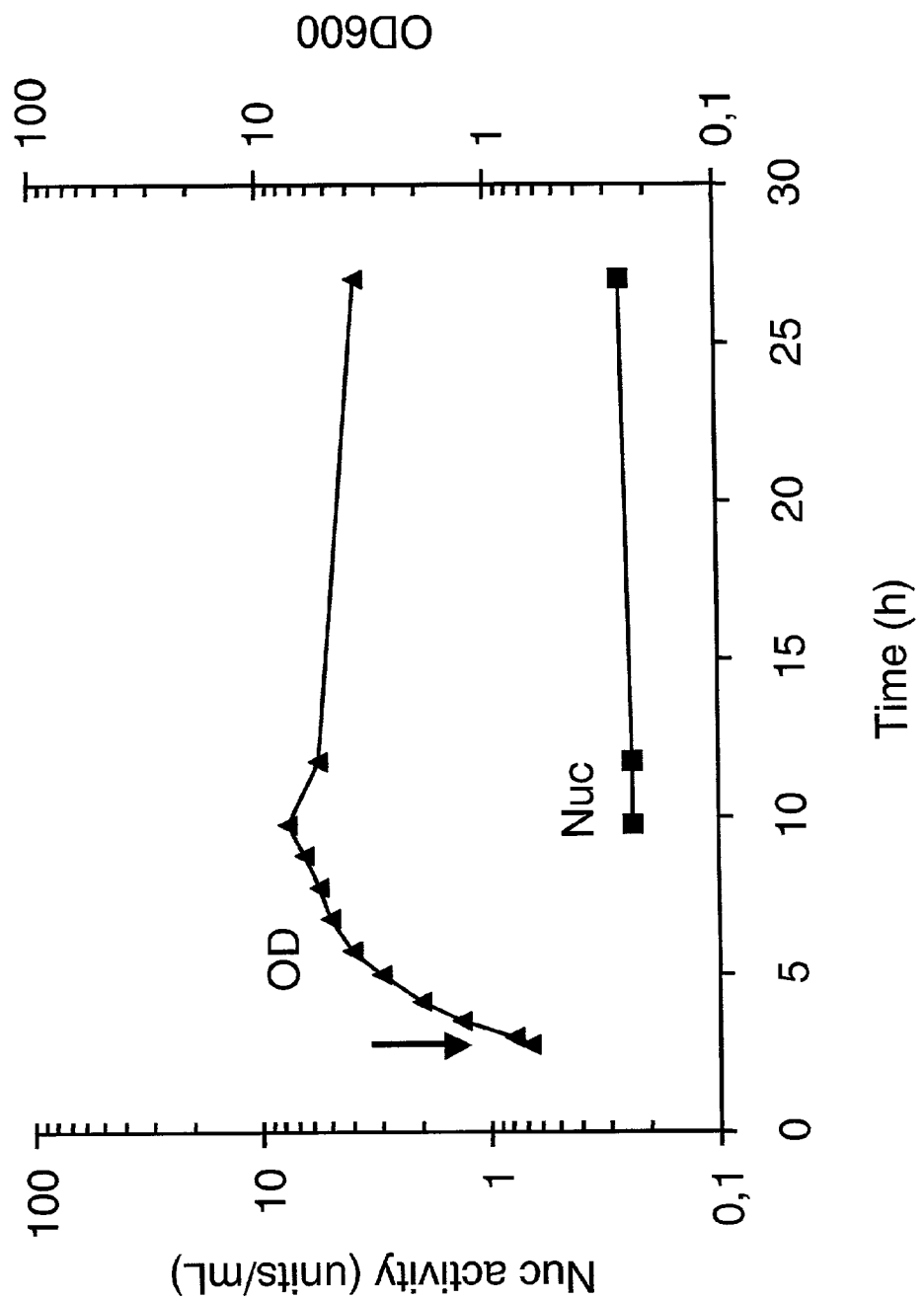
Figure 7A:
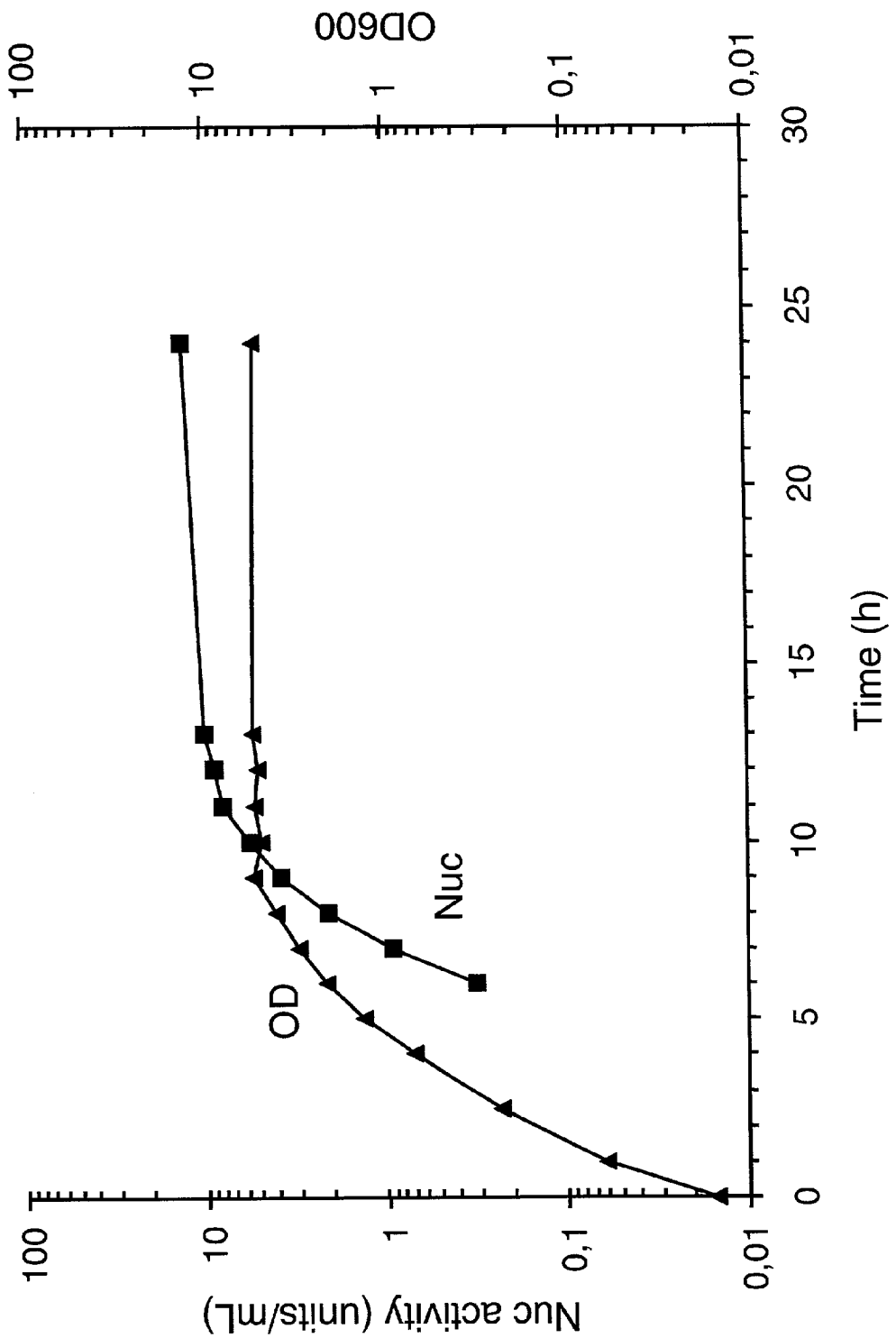
Figure 7B:
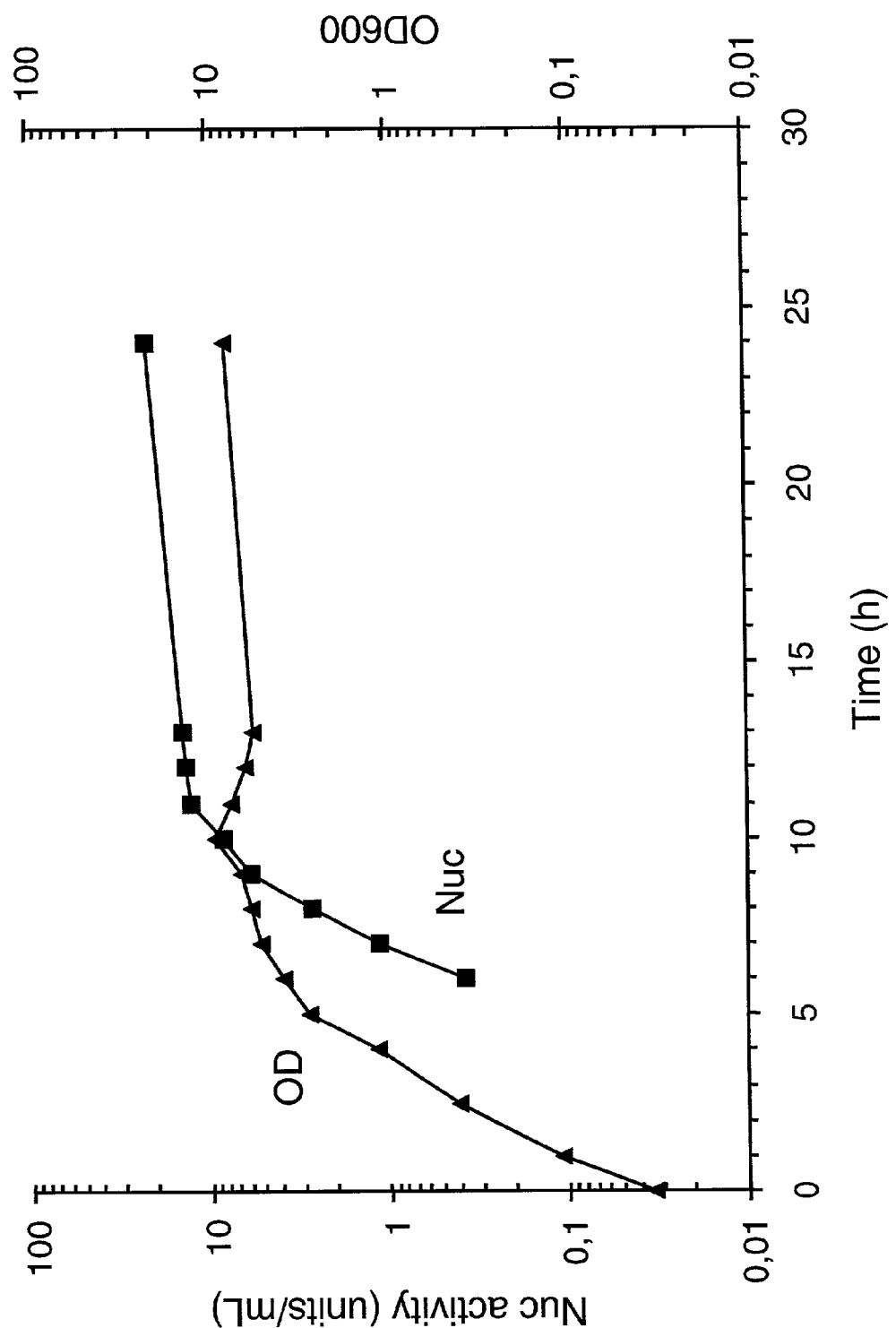
Figure 7C:
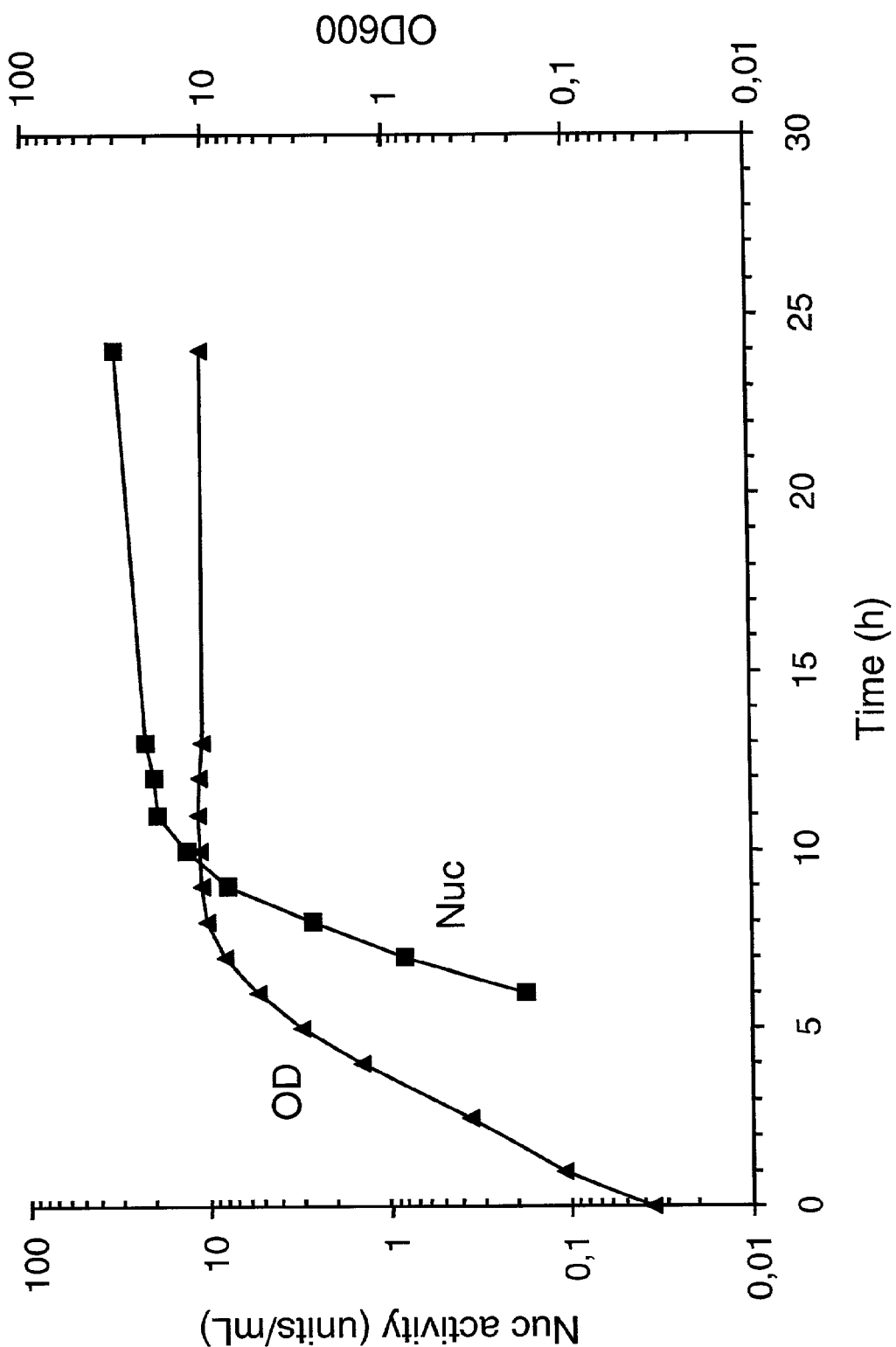
Figure 7D:
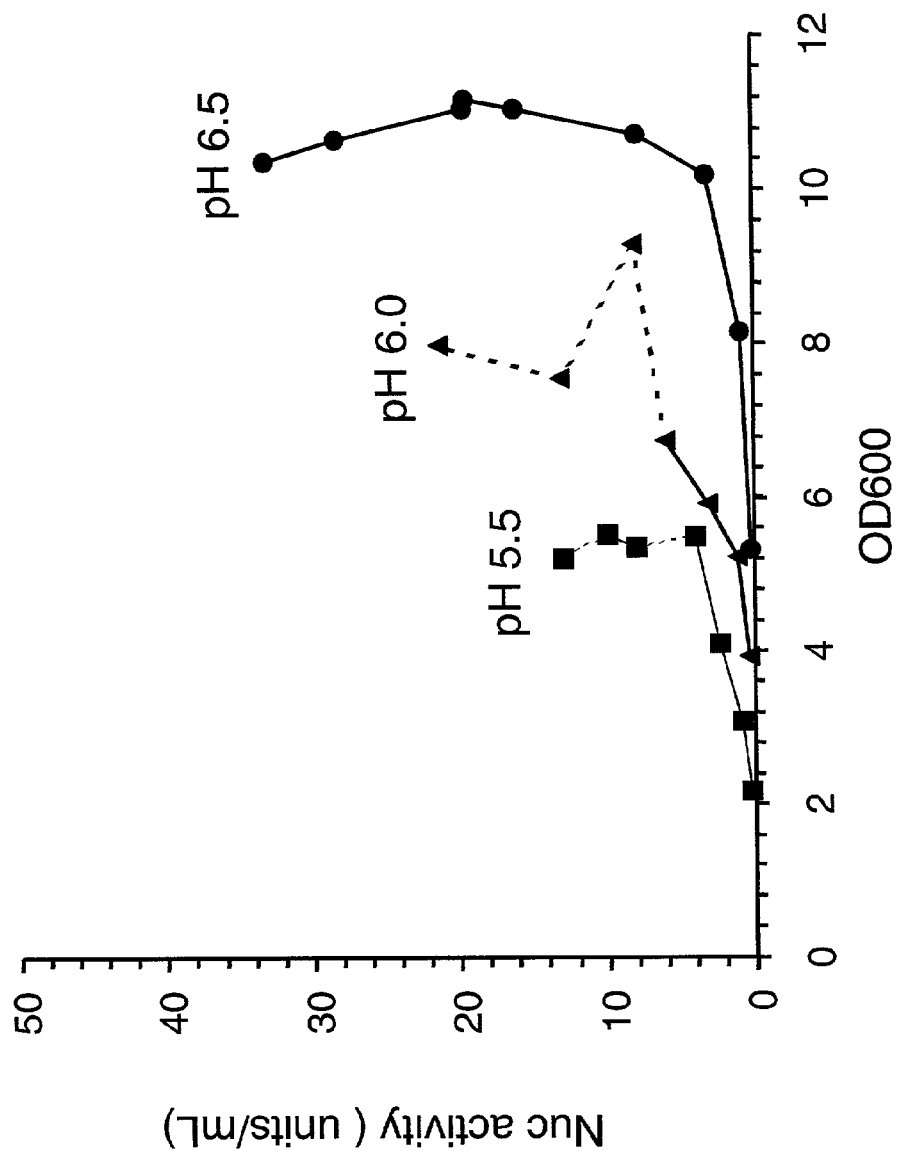
Figure 8:
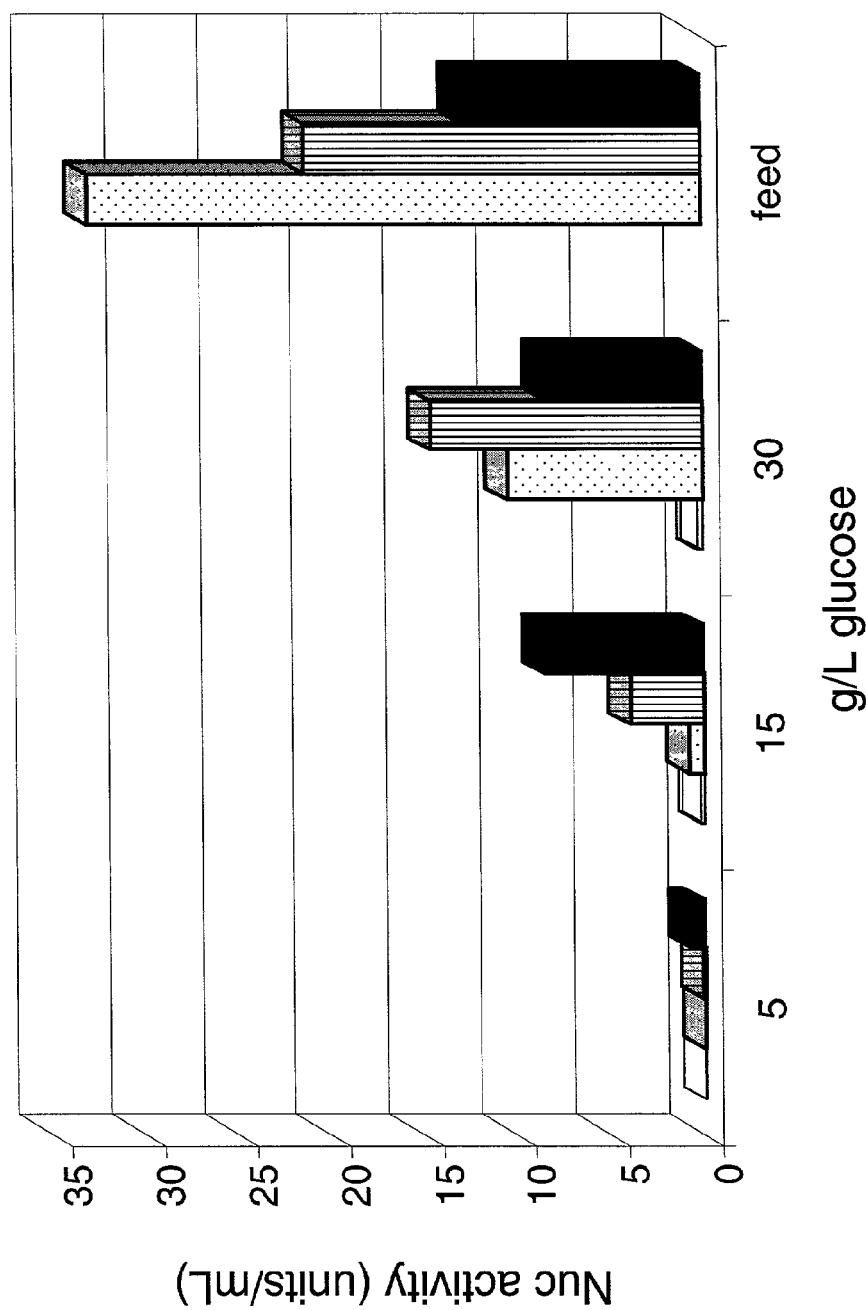
Figure 9A:
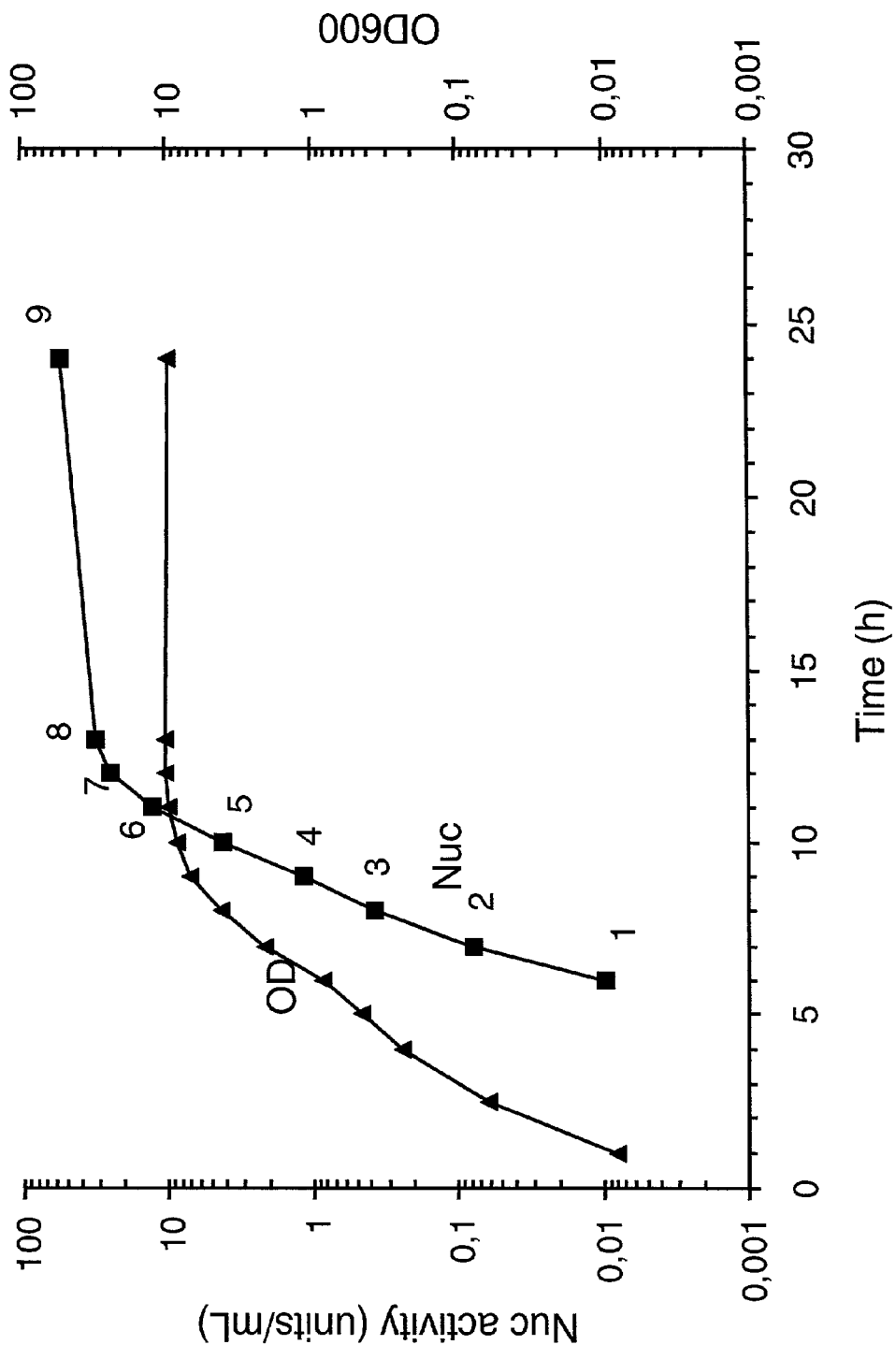
Figure 9B:
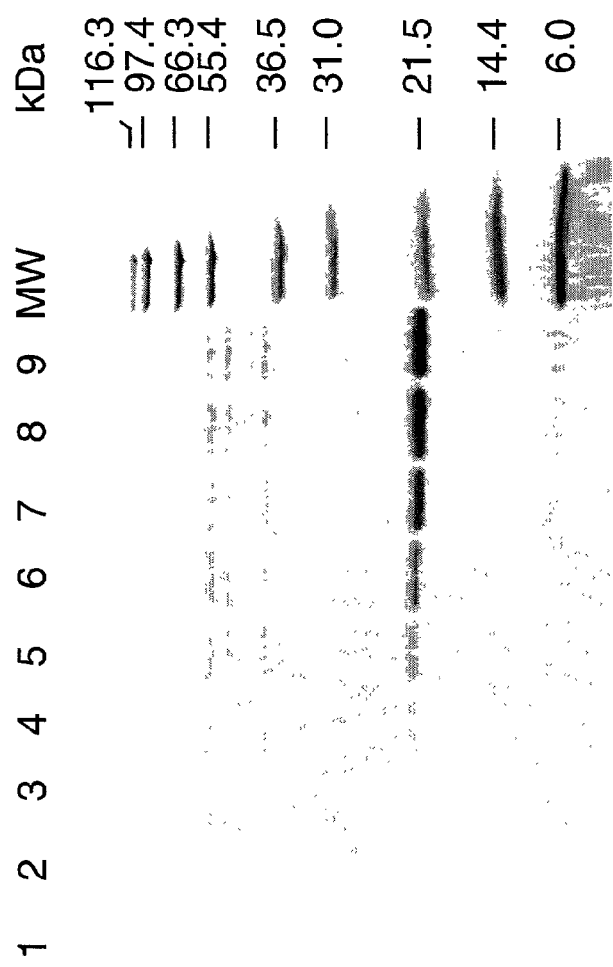

FIGS. 3A-D shows the kinetics of growth (OD600, diamonds) and SNase production (units/ml, squares) by L. lactis strain SMBI111 (medium-copy plasmid, SP310mut2) in LM3-30 medium after fermentation at different pH values. (A) pH 5.5; (B) pH 6.0; (C) pH 6.5; (D) pH 7.0;

FIGS. 4A-B illustrates SNase activity versus $OD_{600}$ for SMBI111 during growth in LM3-15 medium (A) and during growth in LM3-30 medium (B) at pH 5.5 (squares), 6.0 (triangles), 6.5 (circles), and 7.0 (diamonds);

FIG. 5 shows SDS-PAGE analysis of culture supernatants from L. lactis SMBI111 after fermentation in LM3-30 medium at pH 6.5. Lanes 1-9 correspond to the culture samples that were analysed for nuclease activity in FIG. 3C. Ten μl crude culture supernatant was loaded in each lane. Molecular masses (in kilodaltons) are indicated to the right. The triangle indicates the position of the secreted SNase;

FIGS. 6A-C shows induction of P170 by addition of potassium lactate. SMBI111 was grown in LM3-30 medium at pH 7.0. At the time indicated by arrows, when $OD_{600}$ was approximately 0.7, either water (6A), 200 mM potassium lactate (6B), or 200 mM potassium chloride (6C) was added to the culture. $OD_{600}$ is shown as triangles, and nuclease activity (units/ml) as squares;

FIGS. 7A-D illustrates kinetics of SNase production by SMBI111 during fermentations in LM5-5 medium at different pH values (A) pH 5.5. (B) pH 6.0. (C) 6.5. In 7A-7C, $OD_{600}$ is shown as triangles and nuclease activity (units/ml) as squares. 7D shows the SNase activity versus $OD_{600}$ at the different pH values: 5.5, squares; 6.0, triangles; and 6.5, circles. The stippled lines indicate that scatter occurs on the high $OD_{600}$ values. Consequently, some intervening $OD_{600}$ values were omitted in panel D;

FIG. 8 shows final yield of SNase obtained from SMBI111 by fermentation in defined media with different glucose concentration: 5 g/l in LM1-5 with 50 mM NaCl; 15 g/l in LM3-15; 30 g/l in LM3-30; and >70 g/l gradually added to LM5-5 during , and at different pH values: 7.0, white bars; 6.5, dotted bars; 6.0, striped bars; and 5.5, black bars;

FIGS. 9A-B. illustrates fermentation of strain SMBI104 (high-copy plasmid, SP310mut2) in LM5-5 medium at pH 6.5. (A) Kinetics of growth ($OD_{600}$, triangles) and SNase production (units/ml, squares). (B) SDS-PAGE analysis of culture supernatants from SMBI104 after fermentation. Lanes 1-9 correspond to the culture samples that were analysed for nuclease activity in FIG. 9A. 10 μl crude culture supernatant was loaded in each lane. Molecular masses (in kilodaltons) are indicated to the right. The triangle indicates the position of the secreted SNase.

Figure 10:
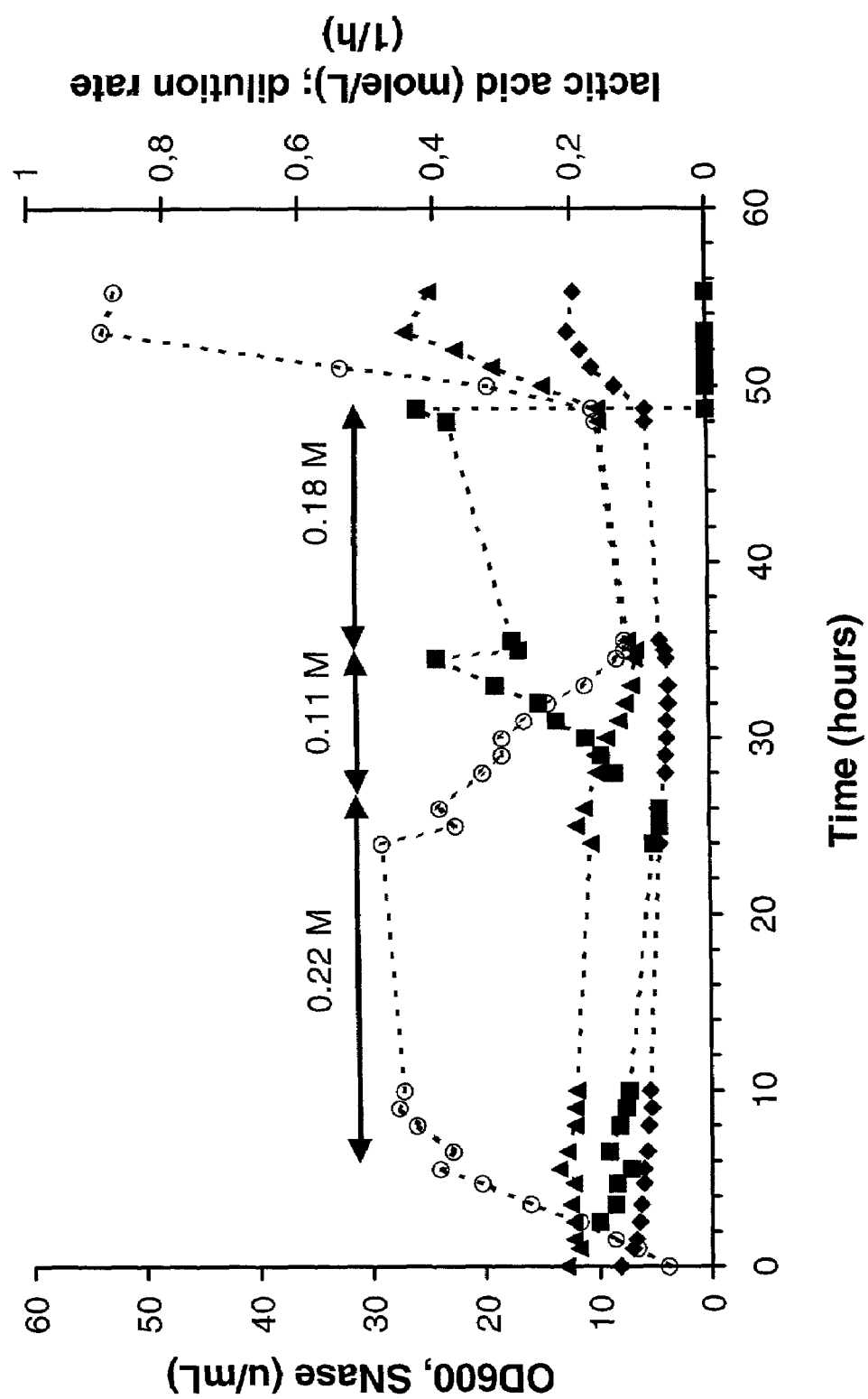

FIG. 10 illustrates cultivation in LM5-50 medium of AMJ627 at pH 6.5 in a phauxostat, where potassium hydroxide and medium were added simultaneously to the fermentor in response to the pH-control unit. During the experiment, the ratio between the amounts of base and medium added to the fermentor was set to different values. The bars indicate the inlet buffering capacity resulting from the different ratios, calculated as number of moles of hydroxide per liter of total volume added (base plus medium). The lactate concentration in the culture is shown as triangles, and the dilution rate is shown as squares. $OD_{600}$ and SNase activity (units/mL) are indicated as diamonds and circles, respectively.

Figure 11:
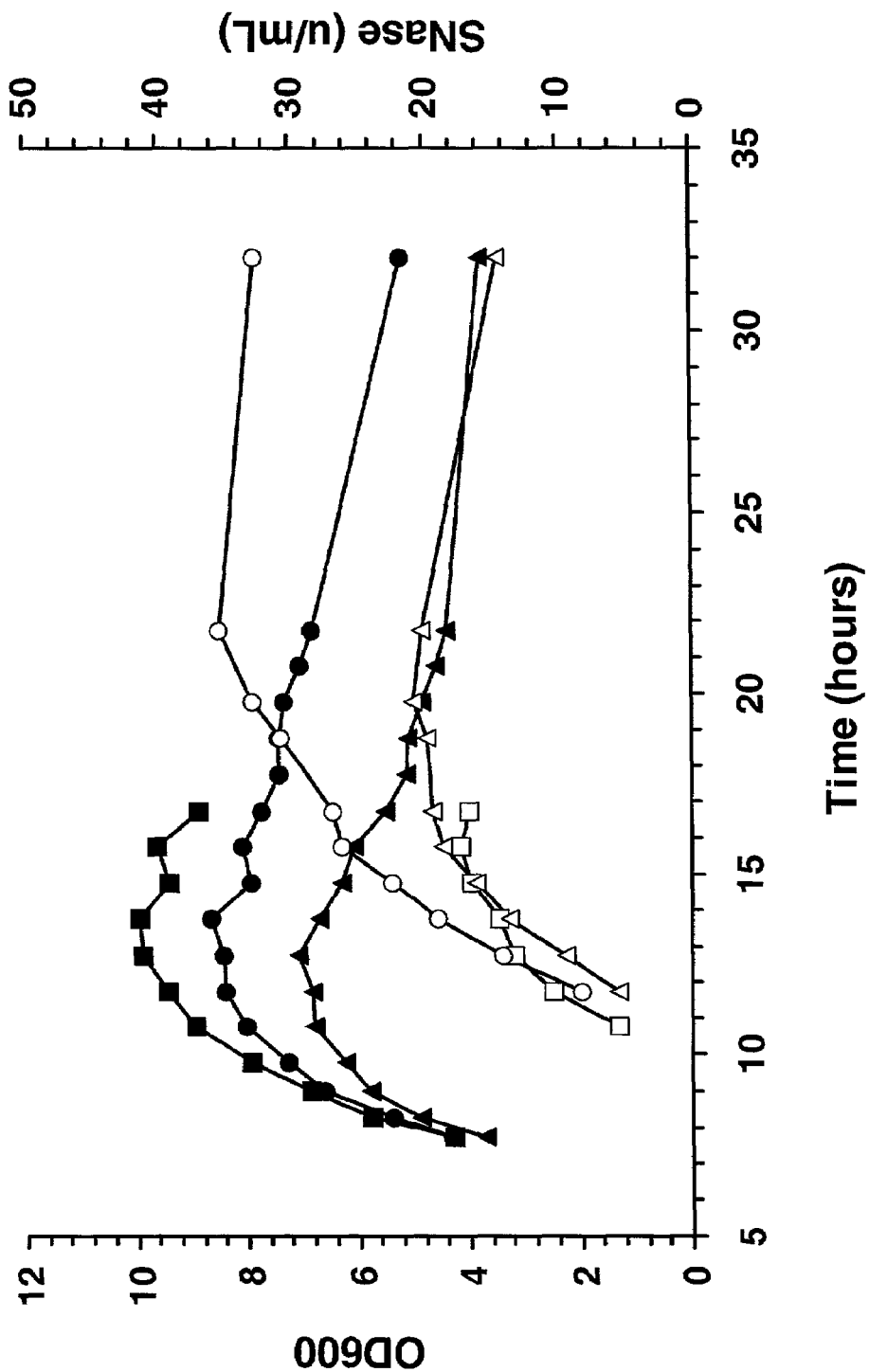

FIG. 11 shows $OD_{600}$ (filled symbols) and SNase activity (open symbols) during short-term chemostat cultivation of SMBI111 at two different rates of medium addition (triangles: 0.14 L/h and circles: 0.07 L/h) compared to a batch culture started in parallel (squares). LM5-50 medium, pH 6.5, was used in all cases.

Figure 12:
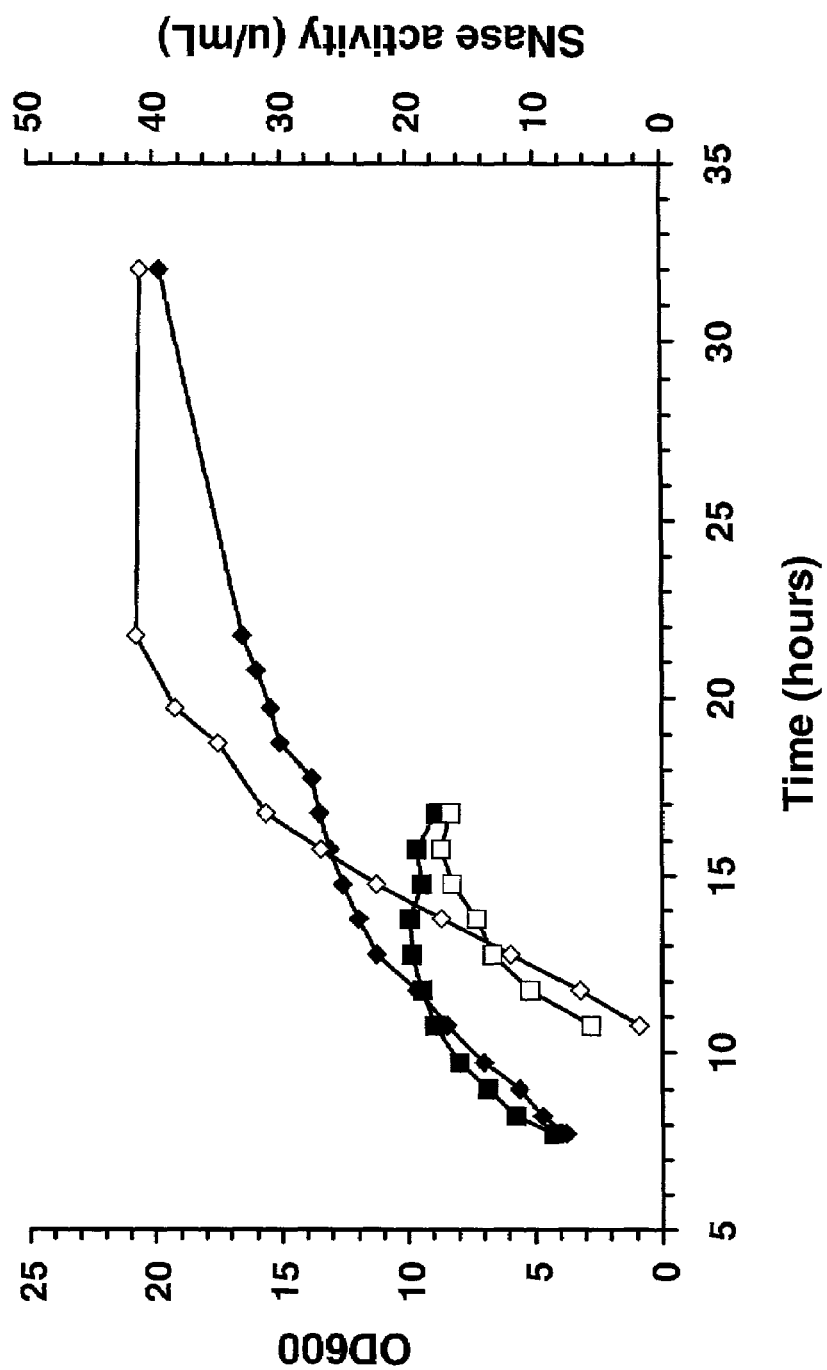

FIG. 12 shows $OD_{600}$ (filled diamonds) and SNase activity (open diamonds) during cultivation of SMBI111 in LM5-50 medium at pH 6.5 with continuous addition of fresh medium and removal of filtrate, while cells were recycled to the culture vessel. Results from a batch culture started in parallel are shown for comparison (squares).

EXAMPLES

Materials and Methods

Bacterial Strains, Plasmids and Growth Conditions

Strains and plasmids used in this study are listed in Table 1.

TABLE 1

| Bacteria and plasmids | Revelant characteristic(s) or DNA insert | Reference or source |
|---|---|---|
| Bacteria | | |
| L. lactis MG1363 | Host for nucleate expression/secretion | Gasson, 1983 |
| E. coli DH10B | E. coli cloning host | Grant et al, 1990 |
| Plasmids | | |
| pHBA102 | Plasmid containingg E. coli transcriptional terminator rrnCtt' | Albrechtsen et al, 1990 |
| pTRKH4 | E. coli-Lactococcus cloning vector, high copy in L. lactis | O'Sullivan & Klaenhammer, 1993 |
| pBS-Nuc | Plasmid containing S. aureus nuclease gene | Le Loir et al, 1994 |
| pΔSPNuc | Signal peptide probe vector containing P170 promoter from pAMJ586 | Ravn et al, 2000 |
| pAMJ586 | Regulated P170 promoter in pAK80 | Madsen et al, 1999 |
| pAMJ752 | Strong regulated P170 promoter variant in pAK80 | Madsen et al, 1999 |
| pNZ1020 | Plasmid containing the Usp45 signal peptide | van Asseldonk et al, 1990 |
| p310mut2 | Plasmid containing the SP310mut2 signal peptide | Ravn et al, unpublished data |
| pSMA610 | Medium copy (MC) expression/secretion vector, promoter from pAMJ586, Usp45 signal peptide | This study |
| pAMJ219 | pSMA610 containing transcriptional terminator rrnCtt' | This study |
| pAMJ325 | High copy (HC) expression vector, promoter from pAMJ752 | This study |
| pAMJ328 | pAMJ325 containing transcriptional terminator rrnCtt' | This study |
| pAMJ166 | pSMA610 containing S. aureus nuclease gene | This study |
| pSMBI91 | HC vector expressing the nuclease, strong P170 promoter, SP310mut2 signal peptide | This study |
| pSMBI93 | MC vector expressing the nuclease, strong P170 promoter, Usp45 signal peptide | This study |
| pSMBI98 | HC vector expressing the nuclease, strong P170 promoter, Usp45 signal peptide | This study |
| pSMBI109 | MC vector expressing the nuclease, strong P170 promoter, SP310mut2 signal peptide | This study |

E. coli strain DH10B (Grant et al., 1990) was grown at 37° C. in LB medium supplemented with 200 µg/ml of erythromycin when appropriate. *Lactococcus lactis* strain MG1363 (Gasson, 1983) was routinely grown at 30° C. in GM17 medium (1.5×M17 with 5 g/L glucose) supplemented, when required, with 1 µg/ml of erythromycin. All flask and fermentor experiments were carried out at 30° C.

To avoid induction of the P170 promoter, pre-cultures were grown in the ArgM17 medium (Madsen et al., 1999), and harvested at an OD600 of 0.5 to 1.0. The cells were washed and concentrated 20-told in cold 20 mM potassium phosphate buffer, pH 6.8. 1 ml aliquots of the suspension were frozen with glycerol (35% final concentration) at −70° C. to be used for inoculation of 1 liter of fermentor medium.

The basal defined medium used for fermentation, LM1, was derived from the SA medium developed by Jensen and Hammer (1993). This latter medium has the following composition (mM or presence/absence in medium):

| Component | Concentration, mM or +/− |
|---|---|
| L-Alanine | 3.4 |
| L-Arginine | 1.1 |
| L-Asparagine | 0.8 |
| L-Cysteine | 0.8 |
| L-Glutamate | 2.1 |
| L-Glutamine | 0.7 |
| Glycine | 2.7 |
| L-Histidine | 0.3 |
| L-Isoleucine | 0.8 |
| L-Leucine | 0.8 |
| L-Lysine-HCl | 1.4 |
| L-Methionine | 0.7 |
| L-Phenylalanine | 1.2 |
| L-Proline | 2.6 |
| L-Serine | 2.9 |
| L-Threonine | 1.7 |
| L-Tryptophan | 0.5 |
| L-Tyrosine | 0.3 |
| L-Valine | 0.9 |
| $NH_4Cl$ | 9.5[a] |
| $K_2SO_4$ | 0.28[a] |
| $KH_2PO_4$ | 1.3[a] |
| Na-acetate | 15 |
| Glucose | 50 |
| MOPS | 40[a] |
| Tricine | 4[a] |
| $CaCl_2$ | 0.0005[a] |
| $MgCl_2$ | 0.52[a] |
| $FeSO_4$ | 0.01[a] |
| NaCl | 50[a] |
| Vitamins[b] | + |
| Micronutrients[a,c] | + |

[a]From Neidhardt et al. J. Bacteriol. 119: 736-747
[b]Vitamins: 0.4 µM biotin, 10 µM pyridoxal-HCl, 2.3 µM folic acid, 2.6 µM riboflavin, 8 µM niacinamide, 3 µM thiamine-HCl and 2 µM pantothenate
[c]Micronutrients: 0.003 µM $(NH_4)_6(MO_7)_{24}$, 0.4 µM $H_3BO_4$, 0.03 µM $CoCl_2$, 0.01 µM $CuSO_4$, 0.08 µM $MnCl_2$ and 0.01 µM $ZnSO_4$ Compared to the SA medium, NaCl, $NH_4$ Cl, tricine and MOPS were omitted in the LM1 medium, the phosphate ($K_2HPO_4$ and $KH_2PO_4$) concentration was increased to 10 mM (from a pH 7 buffer stock solution) and 0.1 mM citric acid was added to prevent precipitation of iron salts. In the media designated LM3 and LM5, all components except phosphate buffer and sodium acetate were increased three and five-fold, respectively. The final figure in the designation of medium indicates the glucose concentration in g/L (e.g. LM1-5 contains 5 g/L glucose). pH was adjusted using HCl, and during fermentation 2 M or 5 M KOH was added automatically to maintain pH. Applikon dished bottom glass vessels of 2 liter total volume were used for 1 liter cultures. Agitation rate was 300 rpm.

Cloning Procedures, Transformation, PCR and DNA Sequencing

DNA manipulations including PCR amplifications and DNA sequencing were performed according to standard procedures (Sambrook et al., 1989). Plasmid DNA from *E. coli* was isolated using the Jet Prep columns (Genomed). *L. lactis* was transformed by electroporation as described by Holo and Nes (1989).

Construction of Plasmids for pH and Growth Phase Controlled Gene Expression and Secretion A pH and growth phase regulated secretion vector for *L. lactis* was constructed by combining the P170 promoter derivative of plasmid pAMJ586 disclosed in WO 98/10079 and Madsen et al., 1999 and deposited under the Budapest Treaty under the accession No. DSM 11137, with the Usp45 signal sequence (van Asseldonk et al., 1990). Plasmid pAMJ586 was digested with BamHI and SalI and the lacLM reporter gene was replaced with a 158 bp DNA fragment containing the lacLM ribosome binding site (Israelsen et al., 1995), the Usp45 signal peptide and an in-frame multiple cloning site comprising BglII, PstI and SalI restriction sites. The PstI site is not unique due to the location of a PstI site in the signal sequence. This 158 bp DNA fragment was synthesized by PCR using pNZ1020 (plasmid harboring the Usp45 signal peptide) as template and the primers Usp primer 1 (5' TAG TAG GAT CCC GGG TCT AGA TTA GGG TAA CTT TGA AAG GAT ATT CCT CAT GAA AAA AAA GAT TAT CTC AGC 3') (SEQ ID NO: 2) and Usp primer 2 (5' ACG CGT CGA CCT GCA GAG ATC TTG TGT CAG CGT AAA CAC C 3') (SEQ ID NO: 3). The PCR product was digested with BamHI and SalI and ligated into pAMJ586, predigested with the same enzymes, resulting in pSMA610.

pSMA610 does not contain a transcription terminator after the multiple cloning site, therefore an E coli transcription terminator, rrnCtt' (Albrechtsen et al., 1990), was PCR amplified using pHBA102 (Albrechtsen et al., 1990) as template and the primers Ter 1 (5' TAG TAG TCG ACA ACC GGG TGT TGG GAG 3') (SEQ ID NO: 4) and rrnctt XhoI (5' GGC CGC TCG AGG GCG CAA AAT AGC GAT 3') (SEQ ID NO: 5). The fragment was digested with XhoI and SalI and inserted into the SalI site of pSMA610. The resulting vector was designated pAMJ219.

A high copy number P170-based expression vector, pAMJ325, was constructed by insertion of a PCR fragment containing the strong P170 promoter derivative from pAMJ752 (Madsen et al., 1999), the lacLM ribosome binding site and a new multiple cloning site into the high copy vector pTRKH4 (O'Sullivan and Klaenhammer, 1993a). Plasmid pTRKH4 was digested with XbaI and subsequently blunt ended with the Klenow fragment. The PCR fragment was obtained by amplification using pAMJ752 as template and the primers pAK80rev2 (5' CCC ATT TAG CCG TCA UTT CAG 3') (SEQ ID NO: 6) and LBEp041 (5' GTC GAC CTG CAG ACT AGT GAT ATC AGA TCT AGC CAT GGG GAA TAT CCT TTC AAA GTT 3') (SEQ ID NO: 7). The PCR fragment was blunt-end ligated into the Klenow treated pTRKH4 to yield pAMJ325. The E. coli transcription terminator, rrnCtt' was inserted into pAMJ325 after PCR amplification using pAMJ219 as template and the primers Ter 1 and rrnCtt' XhoI as described above. The resulting high-copy number expression vector was designated pAMJ328. pAMJ325 and pAMJ328 do not contain a gene encoding a secretion signal.

Cloning of the Staphylococcus aureus Nuclease into the Expression Vectors

To assess the suitability of the expression vectors for secreting the Staphylococcus aureus nuclease (SNase), the NucB gene (Davis et al., 1977; Le Loir et al., 1994) lacking the gene encoding the signal peptide was PCR amplified using two primers Nuc1 (5' GGA AGA TCT TCA CAA ACA GAT AAC GGC 3') (SEQ ID NO: 8) and Nuc2 (5' ACG CGT CGA CGA ATT CGA TCT AAA AAT TAT MA AGT GCC 3') (SEQ ID NO: 9). The underlined sequence of the primers indicates BglII and SalI restriction sites, respectively. These primers were designed to allow PCR amplification of a 567 bp DNA fragment including the coding sequence of the 168 C-terminal amino acids and 63 bp just after the translational stop codon. Plasmid pBS::nuc (Le Loir et al., 1994) containing the entire SNase gene on an 871 bp EcoRI fragment was used as template in a PCR reaction with the primers Nuc1 and Nuc2. The amplified fragment was subsequently digested with BglII and SalI and inserted into pSMA610 resulting in a translational fusion of the nucB gene to the Usp45 signal peptide. The resulting plasmid was named pAMJ166.

In another recent study, we have developed a signal peptide probe vector, pΔSPNuc, which was used to analyse new secretion signals from Lactococcus lactis (Ravn et al., 2000). An optimised signal peptide derivative of SP310, SP310mut2 having the sequence MKFNKKRVAIATFIAL-IFVSFFTISSQDAQAAERS (SEQ ID NO: 1), was inserted into pΔSPNuc resulting in plasmid p310mut2.

To explore the maximum level of nuclease secretion, the strongest P170 derivative located in pAMJ752 (Madsen et al., 1999) was combined with Usp45 and the optimised SP310mut2 signal peptide, respectively. For these constructions, pAMJ166 and p310mut2 were digested with BamHI and SalI, the 900 bp fragment containing the gene encoding the signal peptide and the nuclease gene was purified and ligated to the BamHI-SalI fragment of pAMJ752 containing the P170 promoter, the erythromycin resistance gene and the citrate plasmid replicon (Israelsen et al., 1995) resulting in the plasmids pSMBI93 and pSMBI109, respectively. pSMBI93 and pSMBI109 were transformed into L. lactis resulting in strain SMBI105 and SMBI111.

For investigation of the effect of a higher copy number on nuclease secretion, two nuclease expression plasmids, both based on pAMJ328 were constructed. pSMBI91 and pSMBI98 were constructed by insertion of the 900 bp BamHI-SalI fragments from p310mut2 and pAMJ166 into pAMJ328 similarly digested. Transformation of pSMBI91 nd pSMBI98 into L. lactis resulted in the strains SMBI104 and SMBI106.

Nuclease Activity Determinations

Nuclease activity in culture supernatants was determined by incubation with sonicated salmon DNA as substrate followed by precipitation in ice-cold perchloric acid and subsequent measurement of absorbance at 260 nm ($A_{260}$). 10 μl sample of an appropriate dilution was added to 500 μl of assay buffer (1 mg/ml DNA, 0.1 mg/ml Bovine Serum Albumin, 10 mM $CaCl_2$, 25 mM Tris-HCl pH 8,8) and incubated at 37° C. After 30 minutes, 500 μl of ice-cold 4% (w/v) perchloric acid was added. The larger DNA fragments were allowed to precipitate for 15 to 30 minutes at 0° C. and finally separated from the acid soluble degradation products by centrifugation. $A_{260}$ in the supernatant was measured. To obtain the $A_{260}$ corresponding to "time zero" for each sample, 500 μl assay buffer was mixed with 500 μl 4% PCA at 0° C., 10 μl sample of an appropriate dilution (Dilution buffer: 0.1 mg/ml Bovine Serum Albumin, 10 mM $CaCl_2$, 25 mM Tris-HCl pH 8,8) was added and precipitation performed as described above. One unit of nuclease is defined as the amount of nuclease that will produce 1 μmole of acid soluble polynucleotides from native DNA per minute. The SNase activity in units per ml sample is obtained from $\Delta A_{260}$ by the formula $$\frac{[A_{260}(30 \min) - A_{260}(0 \min)] \times 1.01 \times 100}{10 \times 30}$$

where 10 is the millimolar extinction coefficient at 260 nm for mixed nucleotides and 1.01 is the final volume in ml. To obtain a $\Delta A_{260}$ within a suitable range, high activity samples were diluted to 0.06-0.12 units/ml before the assay was performed.

Protein Characterisation and SDS-PAGE

Culture supernatants were analysed by separation on 12% polyacrylamide gels (NOVEX, San Diego, Calif., US) in SDS-tris-glycine buffer according to the instructions of the manufacturer. The gels were stained in Coomassie Brilliant Blue, R250 (Merck KGaA, 64261 Darmstadt, Germany) according to the manufacturer. The molecular weight marker Mark12™ (NOVEX, San Diego, Calif., US) was used to estimate molecular sizes.

Crude Determination of Relative Copy-number Per Cell of the Medium- and High-copy Number Plasmids Cultures were grown overnight in GM17 medium (1.5× M17 with 5 g/L glucose) at 30° C. Overnight cultures were diluted 20 times in fresh medium and 10 ml samples were collected during cell growth for plasmid extraction. Plasmid DNA was extracted from equal amounts of cells according to the protocol of O'Sullivan and Klaenhammer (1993b). Each plasmid preparation was dissolved in 50 µl Tris-EDTA buffer and analysed by agarose gel-electrophoresis after digestion with SalI.

Example 1

Secretion of S. aureus Nuclease in Flask Culture and Fermentor Culture Using a Nutrient Rich Medium 1.1. Flask Culture Each of the four nuclease expressing plasmids pSMBI91, pSMBI93, pSMBI98 and pSMBI109 was transformed into L. lactis MG1363 and nuclease activity was determined after growth overnight in flasks in GM17 medium. The results are summarised in FIG. 1.

Using the medium-copy number vector, which is based on the pAK80 backbone, the use of the Usp45 signal peptide resulted in about 18% higher yield of secreted nuclease relative to the use of the SP310mut2 signal peptide. This difference is slightly higher, about 23%, when the high-copy number vector pTRKH4 is used for expression. The use of the high-copy vector increased the yield of secreted SNase with a factor of 2.5-3 relative to the medium-copy vector. This increase is consistent with the four-fold higher copy number of pTRKH4 relative to that of pAK80 as determined by agarose gel-electrophoresis (data not shown). This indicates that the use of the high-copy number plasmid does not lead to saturation of the secretion system. These results are in agreement with studies performed by Langella and Le Loir (1999), who demonstrated a positive correlation between plasmid copy number and the yield of secreted SNase.

1.2. Fermentor Culture

In previous experiments where P170 was used to drive the production of an intracellularly located β-galactosidase (Israelsen et al., 1995) a 5-fold higher yield was obtained by cultivation at low pH 5.5 in a fermentor, relative to a flask culture in the same medium. It is likely that this increase in yield is simply a result of the P170 promoter being active over a longer period of time, compared to a flask culture where pH decreases gradually due to the production of lactic acid, and only reaches 5.7 to 5.8 at the very end of growth.

In order to investigate if the use of controlled-pH fermentation would also improve production levels of a secreted product, the nuclease yields obtained from the four nuclease expressing strains grown in GM17 medium at pH 5.5 in fermentors were determined and analysed. To follow the kinetics of induction of gene expression, samples were taken at different $OD_{600}$ values and analysed with respect to nuclease activity. As expected from similar studies with the β-galactosidase, a pronounced growth phase-dependent production of the nuclease was observed in all of the four tested strains (data not shown). For all four strains, the maximum level of secretion was approximately three- to four-fold higher in fermentor experiments, relative to the above flask culture experiments (FIG. 1). Again, the use of Usp45 for SNase secretion was slightly more efficient (~12-17%) compared to the use of SP310mut2. The maximum yield was about 10 units/ml of secreted SNase using the high-copy number vector in combination with the Usp45 signal peptide.

Example 2 pH and Growth Phase Dependent Expression of SNase in a Synthetic Medium Using Batch Fermentation The induction of expression from the P170 promoter at low pH during transition to stationary phase has been demonstrated previously in the nutrient rich GM17 medium (Israelsen et al., 1995; Madsen et al., 1999). This rich medium would not be acceptable for most applications in pharmaceutical production, because some of the components are potential sources of animal viruses, prions or allergenic factors. It would therefore seriously limit the range of applications of the P170 expression system if the regulation of the promoter were dependent on the use of GM17 or another rich medium. The present experiments were designed to determine whether effective expression of heterologous proteins could be achieved using the regulatable P170 expression system in a synthetic, ie defined medium.

As a first test of regulated expression and secretion of SNase from P170 in a synthetic medium, the strain SMBI111 was cultivated in the synthetic medium LM1-5, which is based on the SA medium described in Jensen and Hammer, 1993 (see above). The LM1-5 medium contains the same glucose concentration as does GM17, ie 5 g/L, and 50 mM NaCl was added to compensate for the low solute concentration. Four fermentor cultures were grown in parallel at pH 5.5, 6.0, 6.5 and 7.0, respectively. Supernatants of culture samples taken at intervals from exponential to stationary phase were assayed for nuclease activity. The nuclease production reached 0.81 units/ml at pH 5.5, 0.15 units/ml at pH 6.0 and remained below 0.05 units/ml in the two fermentors maintained at pH 6.5 and 7.0, respectively.

These results clearly demonstrated that the pH regulation is maintained in the defined medium. Furthermore, the nuclease expression occurred during transition to stationary phase confirming an identical regulatory pattern of the P170 promoter in defined and complex media (data not shown).

The results also showed that the production yield was about four-fold lower then the yield achieved using GM17 medium (0.81 units/ml versus 3.11 units/ml, see FIG. 1), whereas the maximum OD was only 25% lower. The physiological and metabolic events accompanying transition to stationary phase is expected to be different in the defined LM1-5 and in the GM17. In the LM1-5 culture, only three hours separated exponential growth from the time when maximum OD was reached and acid production stopped indicating that glucose was exhausted. Only an insignificant amount of nuclease was produced after growth ceased. In GM17, nuclease production occurred during a six-hour period including at least four hours after termination of growth and acid production. It is conceivable, therefore, that the rich medium provides alternative carbon and energy sources, which can support protein synthesis after glucose depletion. It can be concluded from this experiment that the regulatory pattern of the pH and growth dependent expression system observed in a nutrient rich, complex medium like GM17 is maintained in a synthetic or defined medium. However, the yield of heterologous gene product was significantly lower in the defined medium than the yield achieved using a rich medium.

Example 3

Figure 2:
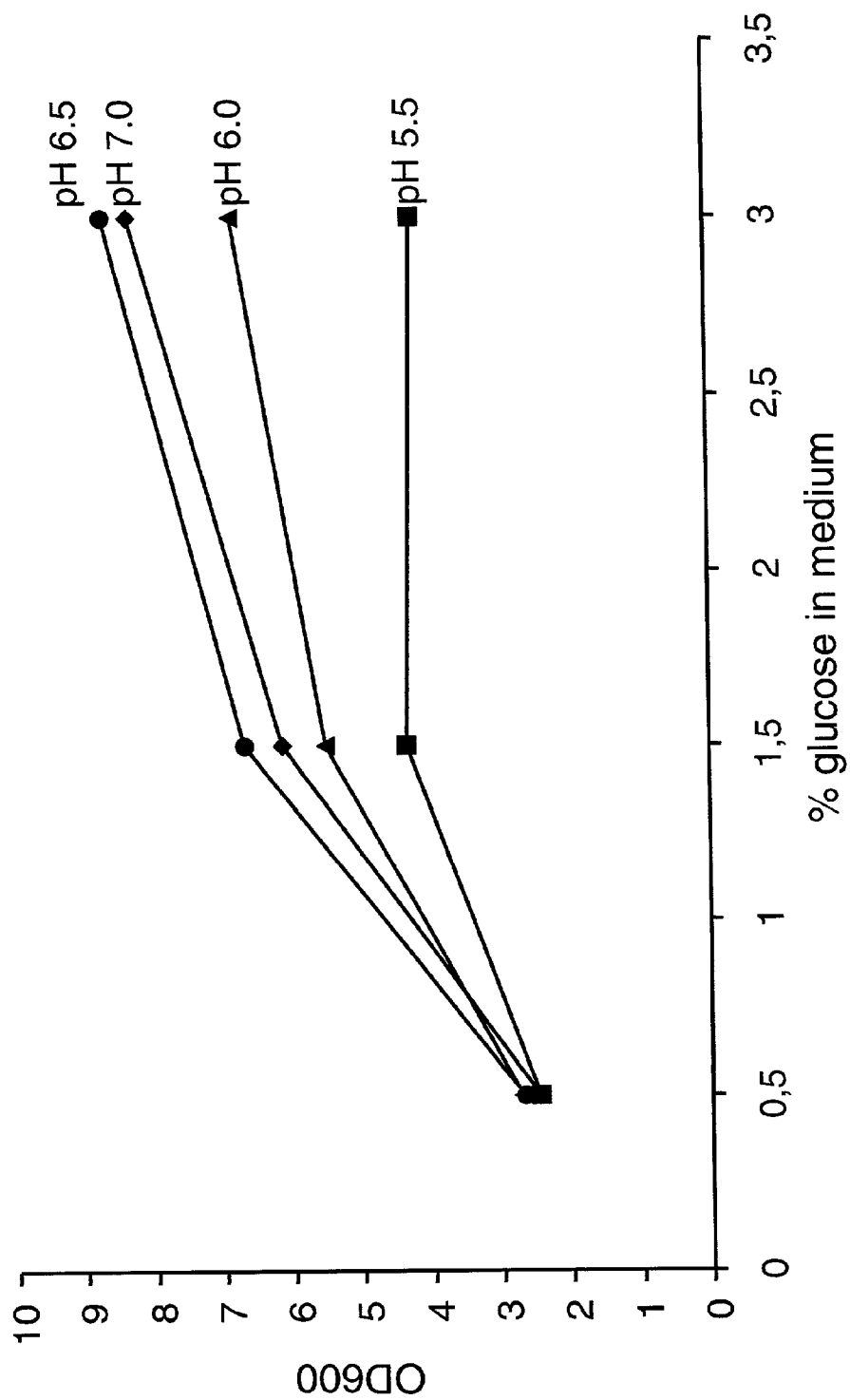
FIG. 2 is a presentation of maximum $OD_{600}$ values obtained from fermentation experiments in defined media with different glucose concentrations and pH values: 5.5, squares; 6.0, triangles; 6.5, circles; and 7.0, diamonds.
Figure 3A:
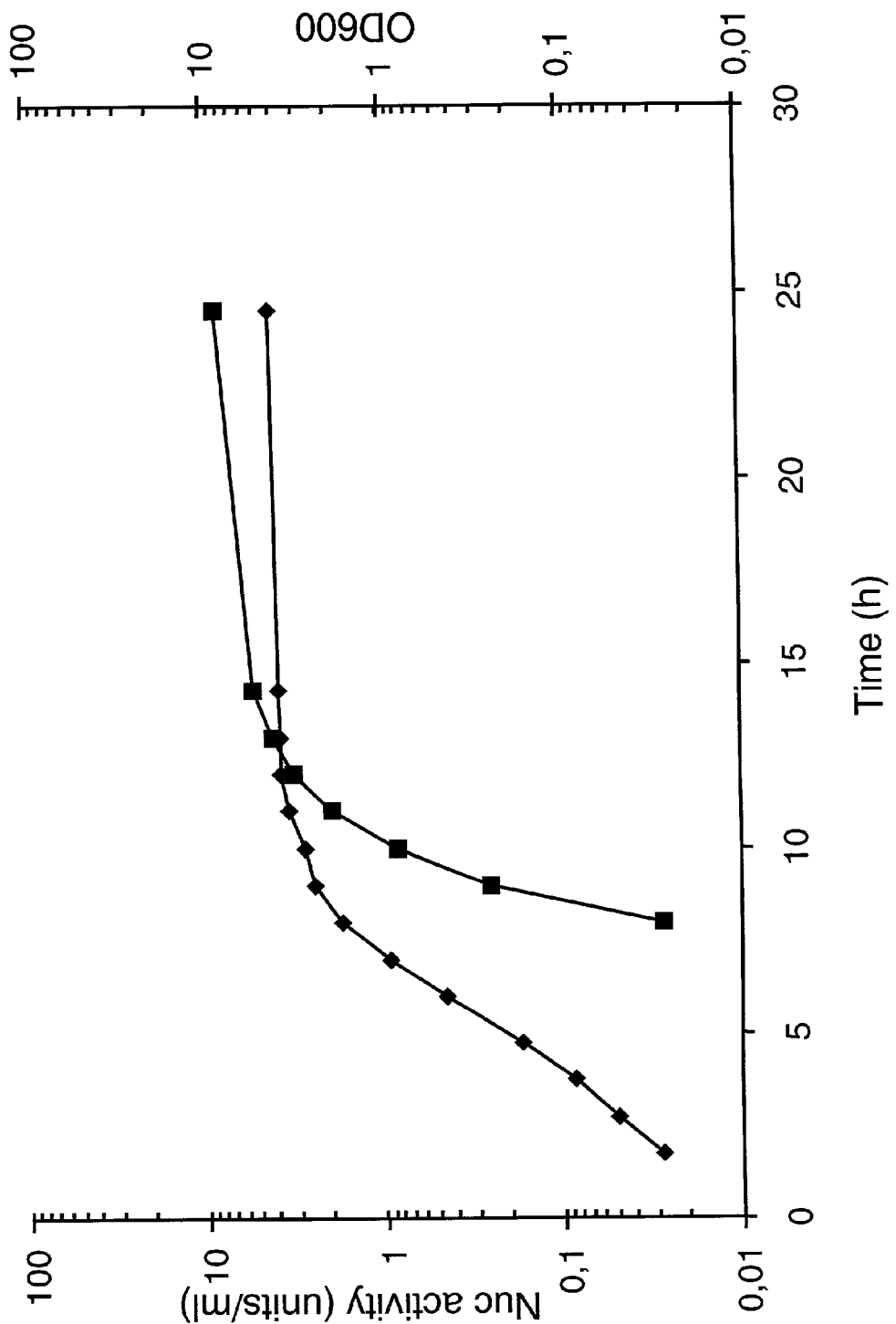
Figure 3B:
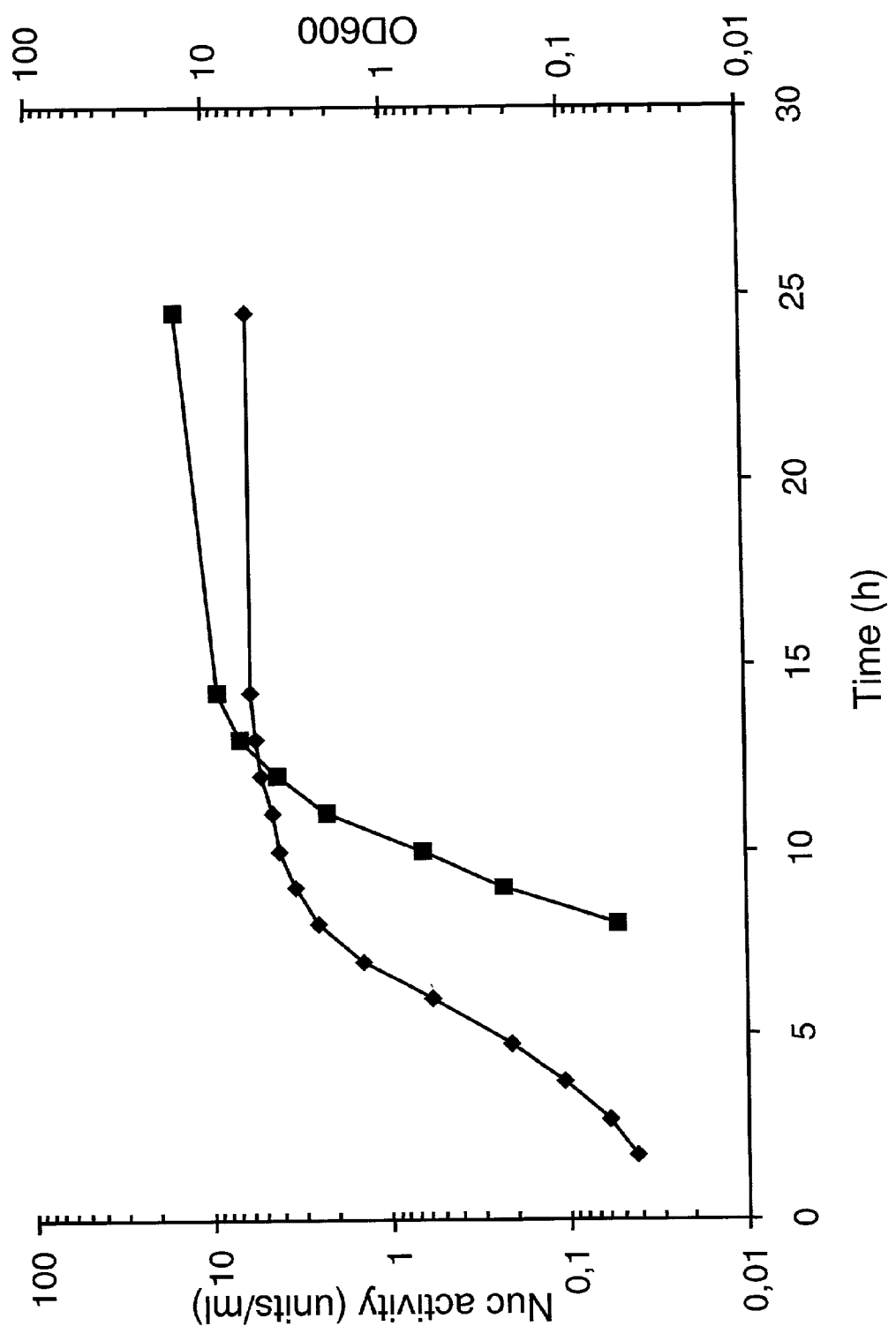
Figure 3C:
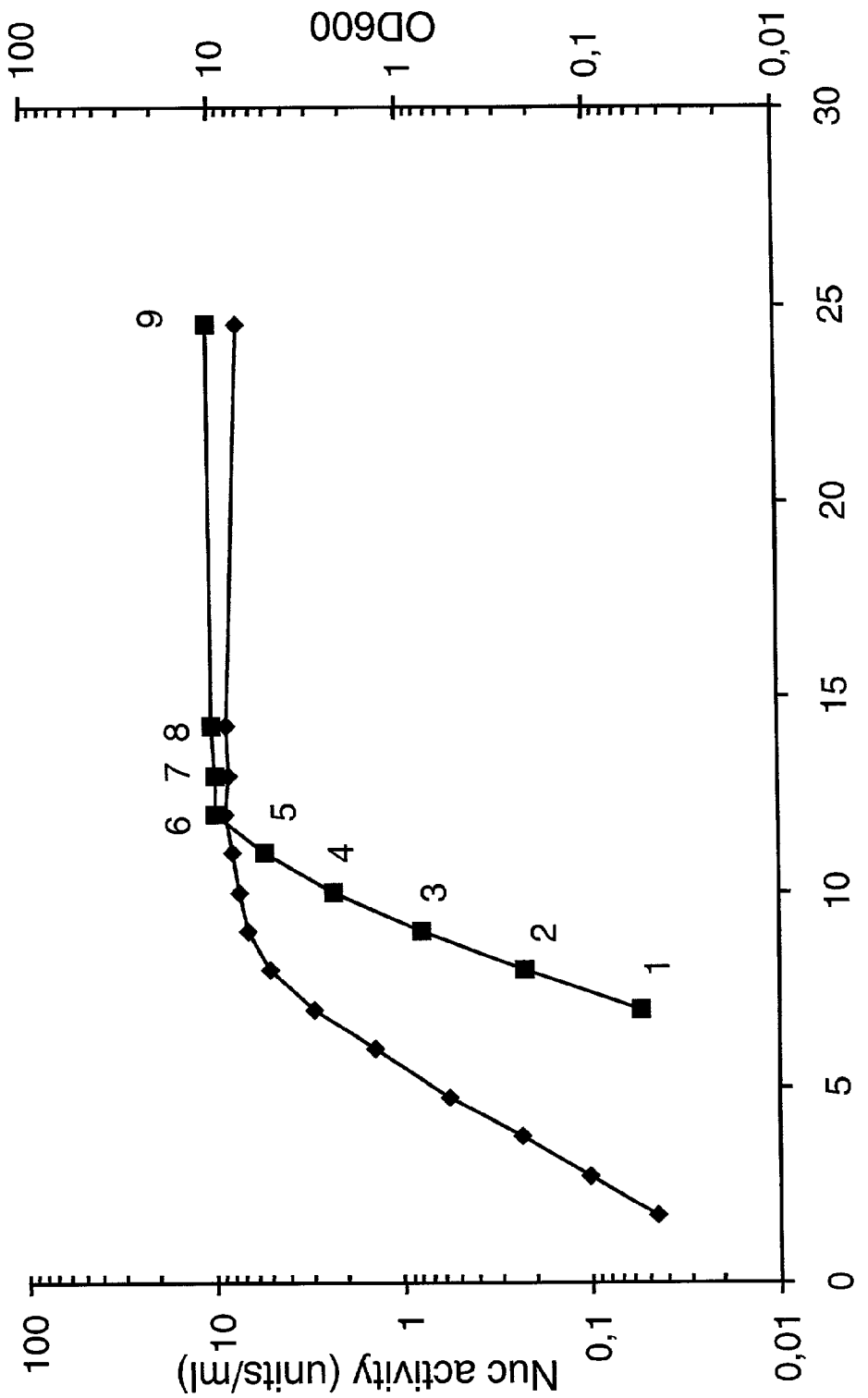
Figure 3D:
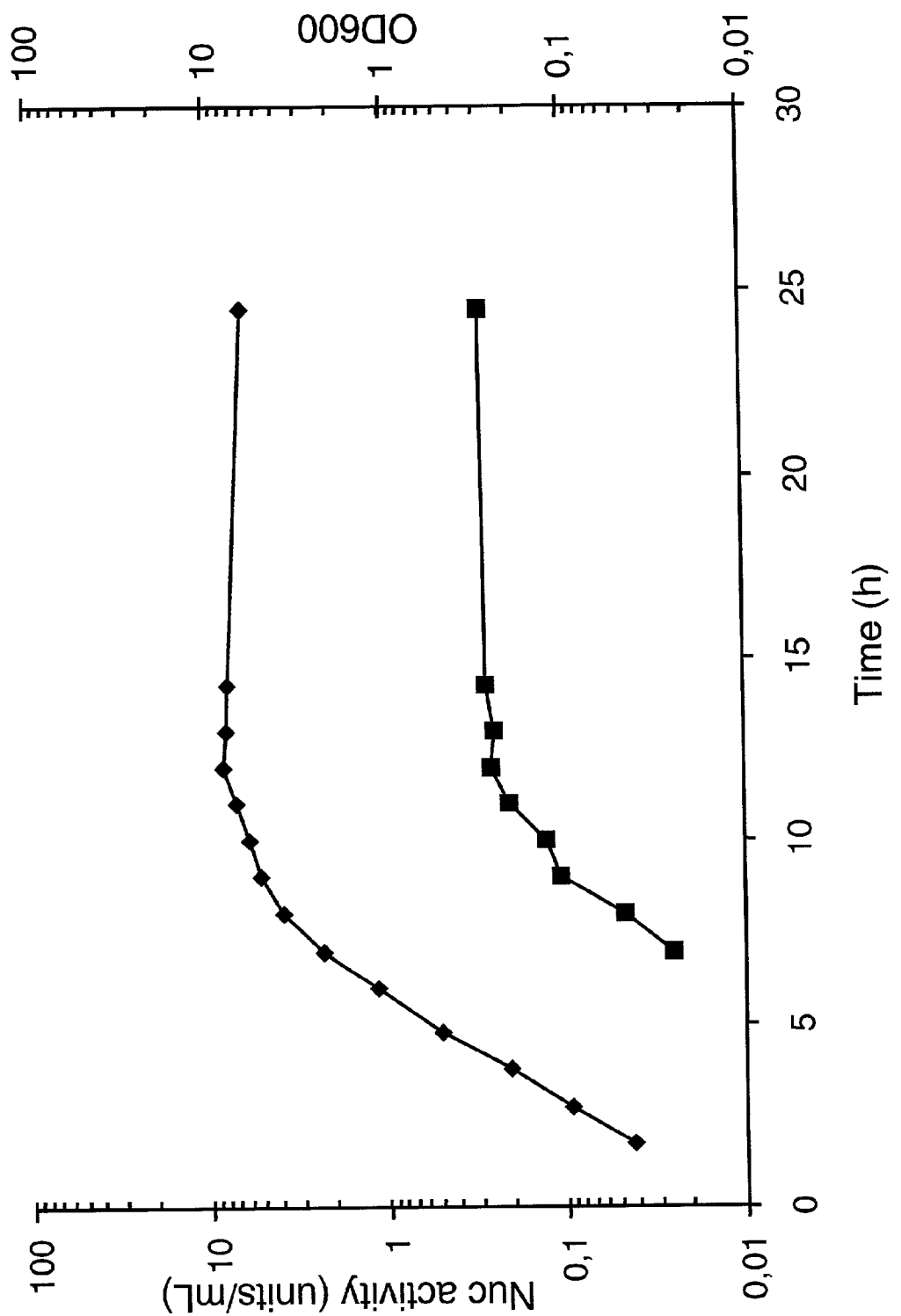

Productivity and Kinetics of the P170 Expression System in a Defined Medium Having a High Substrate Concentration Using Batch Fermentation In this experiment, an attempt was made to improve the yield of SNase by increasing the amount of medium components. Two sets of fermentor experiments were performed, in which the concentration of glucose was raised to 15 g/L and 30 g/L, respectively in the basal medium LM3, ie LM3-15 and LM3-30, see above. Strain SMBI111 was grown in these media at pH 5.5, 6.0, 6.5 and 7.0, respectively. As illustrated in FIG. 2, the final cell densities did not increase in proportion to the glucose concentration. The lack of linear relationship is most pronounced at the lower pH values. This is a well-known phenomenon for lactic acid bacteria, where growth is often inhibited by lactic acid or other metabolic end products before the available carbon source has been exhausted (Kashket, 1987; Loubiere et al., 1997). The inhibitory effect of lactic acid is supposed to be related to the ability of the undissociated acid to diffuse through the cell membrane, causing acidification of the cytoplasm and uncoupling of the membrane potential. The effect becomes more severe at lower pH values, where a larger fraction of the total lactic acid/lactate will be present in the undissociated form. Increasing the glucose concentration will therefore only result in higher biomass yield up to a certain level, which is dependent on the pH (FIG. 2).

Thus, in order to improve production of heterologous proteins such as SNase using the P170 promoter, a balance is required between high biomass yield, which would require a high pH, and high P170 promoter activity, which should be optimal at pH below 6.0. Interestingly, however, SNase production also occurred in the more concentrated medium, LM3-30, at pH 6.0 and 6.5, while SNase expression was still repressed at pH 7.0 (FIGS. 3A-D). The growth phase dependency was clearly observed at pH 5.5, 6.0 and 6.5 (FIGS. 4A-B). It was also observed that the cell density at which P170 induction occurred was higher at higher pH values. It might even be expected that SNase would be produced at pH 7.0, if the glucose concentration was increased sufficiently.

The production of SNase in the LM3-30 medium at pH 6.5 was analysed by SDS-PAGE (FIG. 5). The 22 kDa protein band of SNase was clearly detected after the transition to stationary phase (FIG. 5, lane 5). The supernatant appears to contain only a small amount of other proteins.

The results of these experiments also showed that increasing the glucose concentration in the defined from 5 g/L (see Example 2) to 15 g/L resulted in a significant increase in yield of gene product. It was also observed that a further increase in glucose concentration, ie from 15 to 30 g/L in the LM3 medium resulted in an increased yield of SNase at pH 6.0 and 6.5 of 3.7 and 12-fold, respectively.

Example 4

Induction, in a Batch Fermentation Process, of SNase Production in the P170 Expression System by Addition of Potassium Lactate The results presented in FIGS. 3 and 4 suggested that lactic acid might induce P170. The concentration of lactic acid is strongly correlated with the cell density in the culture. The inhibitory effect of lactate on cell growth and the induction of P170 are both pH dependent. Three parallel fermentations in LM3-30 medium were carried out, all kept at pH 7.0. At $OD_{600} \approx 0.7$-0.8, potassium lactate (pH 7.0) or potassium chloride was added to a final concentration of 200 mM. This concentration of lactate will normally be reached at $OD_{600} \approx 7$ in LM3-30 medium. Addition of both salts reduced the growth rate slightly, but only the addition of potassium lactate induced SNase production (FIGS. 6A-C). This shows that P170 activity in *L. lactis* is induced by lactate. From a practical point of view, lactate addition may be used for induction of expression under conditions that would otherwise not be optimal for P170 promoter activity.

Example 5

Further Increase of Gene Product Yield in the P170 Expression System by Increasing the Level of Available Substrate Using a Fermentation Process As shown in Example 3, the yields of SNase at pH 6.0 and 6.5 were increased 3.7 and 12-fold, respectively by increasing the glucose concentration from 15 to 30 g/L in the LM3 medium in a batch fermentation process.

Further optimisation could be expected to include the use of even higher glucose concentrations. In batch fermentation experiments using other strain constructions based on the P170 expression system it was previously observed that an increase of glucose concentration to 50-80 g/L resulted in higher yields of gene product. However, the fermentation time was also prolonged due to slow growth probably caused by osmotic stress (data not shown). To avoid this, a fermentation system was set up for the gradual addition of glucose. A pump for addition of a concentrated glucose solution (500 g/L) was connected to the base pump output of the fermentor's pH controller. In this set-up, glucose is added in parallel with addition of KOH for pH regulation. The glucose supply followed the rate of acid production in the culture and was strictly correlated to cell density and demand for substrate. The concentration of other medium components (except acetate and phosphate) was increased five-fold compared to LM1 to prevent nutrient depletion at high cell densities. The initial concentration of glucose was 5 g/L (LM5-5 medium).

SMBI111 was inoculated into three fermentors containing LM5-5 medium, which was adjusted to pH 5.5, 6.0 and 6.5, respectively. Glucose addition started when acid production resulted in pH reduction, and the rate of addition increased during active growth. In all cultures, acid production and glucose addition continued after the maximum OD was reached. A large part of the total yield of SNase was produced in this phase (FIGS. 7A-D). At each pH, the total yield of SNase was improved compared to the batch fermentation. The final SNase yields at different pH values in the different media are summarised in FIG. 8. It is clearly seen that the lowest pH value was optimal for SNase production at low glucose concentrations, and that this pattern changed gradually as glucose concentrations were increased. In these fermentations the highest SNase yield, ie 33.1 units/ml, was obtained at pH 6.5.

Example 6 pH Controlled Fermentation with High Copy-number Vector Strain Containing the P170 Expression System Strain SMBI104, containing the high copy-number plasmid pSMBI 91, was grown in a fermentor under the conditions that showed the highest amount of SNase in strain SMBI111 (medium copy-number plasmid), i.e. LM5-5 medium with pH-controlled glucose feed at pH 6.5 (FIGS. 9A-B). The final yield that was achieved was 54 units/ml, ie 64% higher than that obtained from SMBI111 (33 units/ml), indicating that the effect of copy number may not be as strong under these conditions as in GM17. It is likely that bottlenecks in the expression machinery or in the secretion system are responsible for the lack of higher yields when using the high-copy number plasmid in the fermentation. As it appears from FIG. 9B, the supernatant obtained from the LM5-5 medium growth in this experiment appeared very pure with only a few contaminating host proteins. Generally, the amount of heterologous product (SNase) exceeded 50% of the total protein present in the supernatant and the use of only one or a few purification steps should therefore result in a pure pharmaceutical-grade product.

The maximum production capacity that was obtained in these experiments using the P170 expression system in *Lactococcus lactis* under fermentation conditions was 54 units of secreted SNase pr. ml culture supernatant. Based on a preliminary determination of the specific activity of SNase (approx. 550 units/mg) this activity corresponds to approx. 100 mg/L of secreted SNase. Is it difficult to compare the efficiency of different gene expression systems due to the use of different gene products as reporters for protein production. However, recently Langella and Le Loir (1999) described the use of the same SNase for secretion studies in *L. lactis*. Using a strong constitutive promoter and a synthetic propeptide in a high-copy number vector these authors obtained 10-25 mg/L of secreted SNase in flask experiments using a rich medium.

Example 7

Further Improvement of Gene Product Yield Obtained with the P170 Expression System in a Fermentation Process In our efforts to possibly increase the production capacity further experiments similar to the experiments i Example 6 were carried out, but where the LM5-5 medium was supplemented with yeast extract at an amount in the range of 1 to 10 g/L. At an amount of 5 g/L of yeast extract, the yield of secreted SNase increased to 123 units/ml, which corresponds to approx. 225 mg/L SNase. This is to our knowledge the highest amount of secreted heterologous protein reported to date for lactic acid bacteria.

Example 8

Prolonged Production Phase by use of Continuous Cultivation Set-up.

In the batch and fermentations described in Examples 1-7, synthesis of the heterologous product would eventually cease, either from lack of glucose or from accumulation of metabolic products (primarily lactic acid). By applying various methods of continuous cultivation it was possible to prolong the production phase. Three different methods were tested in short-term experiments with SMBI111 or strain AMJ627 in LM5-50 at 30° C. and pH 6.5. The first two experiments were carried out as a phauxostat and a chemostat cultivation. The third experiment included a cell recycle fermentation, i.e. cultivation at a constant culture volume with a constant inlet of fresh medium and an outlet of culture medium through a filter unit.

8. 1 Phauxostat-cultivation

The phauxostat set-up included a one-liter working volume fermentor, a 10 L reservoir of fresh LM5-50 medium and a reservoir of 5 molar potassium hydroxide. Pumps for addition of base and medium to the fermentor were turned on and off simultaneously in response to the pH-controller. A third pump was used to keep a constant volume in the fermentor vessel by draining overflow from a level tube. The medium and buffer reservoirs were placed on electronic balances, which were used to monitor the added amounts. The dilution rate was calculated from these values. The ratio between in-flow of base and medium could be varied by changing the flow-rate of the medium addition pump. Thereby it was possible to control the number of moles of potassium hydroxide per liter of total volume added. This number corresponds to the buffering capacity of the medium, $BC_R$, in the original description of the phauxostat method by Martin and Hemfling (1976). The lactic acid concentration in a *Lactococcus lactis* phauxostat culture is expected to approach the same value.

The strain used for this experiment, AMJ627, was MG1363 carrying the plasmid pAMJ166. This strain is similar to SMBI111, but contains the Usp45 signal peptide and the AMJ586 derivative of P170 instead of SP310mut2 and the AMJ752 derivative.

FIG. 10 shows $BC_R$, lactate concentration, dilution rate, optical density, and SNase activity. After an initial phase of adjustment, $BC_R$ was set to 0.22 mole/L. Lactate concentration increased to 0.20-0.23 mole/L, and SNase activity increased to 20-30 units/mL. However, the optical density and the dilution rate were decreasing steadily during this phase. Presumably, growth inhibition was due to production of lactate.

After 20 hours of operation at a $BC_R$ of 0.22 mole/L, the value was reset to 0.11 mole/L. The lactate concentration decreased and dilution rate gradually increased. During the next 8.5 hours $OD_{600}$ was stabilised at a slightly lower value and SNase activity decreased gradually to 8 units/mL. When $BC_R$ was readjusted to 0.18 mole/L, dilution rate immediately decreased but increased again during the following 14 hours, while the SNase level increased slightly to 10 units/mL.

A total volume of 10 L fresh medium was added. When addition of medium was stopped, the culture was allowed to grow to stationary phase. The final SNase activity was higher than in a parallel batch culture in the same medium, 53 units/mL vs. 27 units/mL.

Although the process did not reach a steady state during this experiment, it was clear that both growth and productivity of the culture reacted to changes in the ratio between medium and potassium hydroxide fed to the fermentor. A relatively high SNase level was reached at a buffering capacity of 0.22 mole/L, but under these conditions growth rate and dilution rate were decreasing. When the buffering capacity was first reduced to 0.11 mole/L and then increased again to 0.18 mole/L a higher dilution rate but a lower SNase level was obtained. An optimal value of buffering capacity might be found between 0.18 and 0.22 mole/L.

8.2 Cultivation in Chemostat

SMBI111 was grown in three one-liter fermentors with pH kept at 6.5 by addition of 3 M potassium hydroxide. At an $OD_{600}$ value of approximately 5, addition of medium to two of the fermentors was started at different rates, 0.07 and 0.14 L/h. The volume was kept constant by a pump draining off culture from a level tube.

Optical density and SNase activity in the cultures are shown in FIG. 11. The batch culture reached a maximum $OD_{600}$ of 9.9 within 14 hours and stopped producing acid at 16 hours. SNase activity was 17 units/mL at the end of fermentation. The two continuous fermentations were allowed to run for 16-17 hours more, resulting in an overall medium throughput of 1.65 L and 3.0 L, respectively. The maximum optical density was lower in both cases than in the batch culture, and the decrease in OD that followed showed that the specific growth rate was lower than the dilution rate (FIG. 11). However, the SNase level continued to increase for at least six hours after the maximum OD had been reached, and was only reduced by 10-20% when addition of medium was stopped 10 hours later. The overall nuclease activity in the fermentor culture plus the culture collected from the outlet is shown in the table below. (Some additional production may have taken place in the collected culture.)

TABLE 2

| SNase activity (units) in: | Batch | Continuous, 0.07 L/h | Continuous, 0.14 L/h |
|---|---|---|---|
| Fermentor vessel | 20,000 | 33,000 | 17,000 |
| Collected outlet |  | 40,000 | 40,000 |
| Total activity | 20,000 | 73,000 | 57,000 |
| Units/L medium | 20,000 | 27,500 | 14,300 |
| Duration (hours) | 16 | 32 | 32 |
| Units/hour | 1,250 | 2,280 | 1,780 |

Both continuous fermentations resulted in a higher overall yield of SNase than the batch culture. At the highest dilution rate, yield per liter of medium was lower than in the batch culture. However, depending of the cost of working hours in the fermentation facility compared to the cost of medium, the continuous process may still be advantageous compared to a series of batch processes, which would be separated by down-time for medium preparation and for cleaning and sterilization of equipment.

In both cases, the cell density decreased after the first 14-15 hours and productivity was reduced after 32 hours. This was probably caused by inhibition from lactate produced in the culture. For obtaining a stable production at a higher density it would be necessary to reduce the glucose concentration in the inlet medium to a value where less lactic acid can be produced.

8.3 Cultivation with Cell Recycle and Continuous Replacement of Medium

In the chemostat experiments as described above, the production capacity was reduced due to continuous removal of culture from the vessel. This was avoided by recycling the cells to the vessel.

A device for tangential flow filtration (Vivaflow 50, 0.2 μm, Vivascience) was connected to a one-liter fermentor through silicone tubing. SMBI111 was grown in LM5-50 medium at pH 6.5 in the fermentor. At an optical density of approximately 5, addition of fresh LM5-50 medium to the culture was started at a rate of 0.13 L/h. At the same time, tangential flow filtration of medium from the culture was started. The retentate flow, which was recirculated to the fermentor, was 40-45 mL/min, and the filtration rate, approximately 2 mL/min, was adjusted to keep the culture volume constant.

A total volume of 3 L of medium was fed to the culture within 24 hours. During this time the optical density increased to 19.8, and the SNase activity increased to 41 units/mL (FIG. 12). The overall yield of SNase was 112,000 units including 71,000 units in the collected filtrate.

In this case, where the production cells are not lost from the culture, it should be possible to continue the process until, eventually, filtration would be hampered by high cell density or physiological limitations would prevent further growth and SNase production. Further improvement of productivity could be achieved by optimization of culture pH, substrate concentration and flow rates.

REFERENCES

Albrechtsen B, Squires C L, Li S and Squires C (1990) Antitermination of characterized transcriptional terminators by the *Escherichia coli* rrnG leader region. J Mol. Biol. 213:123-134.

Davis A, Moore I B, Parker D S and Taniuchi H (1977). Nuclease B. A possible precursor of nuclease A, an extracellular nuclease of *Staphylococcus aureus*. J. Biol. Chem. 252:6544-6553.

de Ruyter P G, Kuipers O P and de Vos W M (1996). Controlled gene expression systems for *Lactococcus lactis* with the food-grade inducer nisin. Appl. Environ. Microbiol. 62:3662-3667.

Djordjevic G M and Klaenhammer T R (1998). Inducible gene expression systems in *Lactococcus lactis*. Mol. Biotechnol. 9:127-139.

Gasson M J (1983) Plasmid complements of *Streptococcus lactis* NCDO712 and other lactic acid streptococci after protoplast-induced curing. J. Bacteriol. 154:1-9.

Grant S G, Jesse J, Bloom F R and Hanahan D (1990). Differential plasmid rescue from transgenic mouse DNAs into *Escherichia coli* methylation-restriction mutants. Proc. Natl. Acad. Sci USA 87:4645-4649.

Holo H and Ness I F (1989). High-Frequency Transformation, by Electroporation, of *Lactococcus lactis* subsp. *cremoris* Grown with Glycine in Osmolytically Stabilized Media.Appl. Environ. Microbiol 55:3119-3123.

Israelsen H and Hansen E B (1993). Insertion of Transposon Tn917 Derivatives into the *Lactococcus lactis* subsp. *lactis* Chromosome. Appl. Environ. Microbiol. 59:21-26.

Israelsen H, Maden S M, Vrang A, Hansen E B and Johansen E (1995). Cloning and partial characterization of regulated promoters from *Lactococcus lactis* Tn917-lacZ integrants with the new promoter probe, pAK80. Appl. Environ. Microbiol 61:2540-2547.

Jensen P R and Hammer K (1993). Minimal Requirements for Exponential Growth of *Lactococcus lactis*. Appl. Environ. Microbiol. 59:4363-4366.

Kashket E R (1987). Bioenergetics of lactic acid bacteria: cytoplasmatic pH and osmotolerance. FEMS Microbiol. Lett. 46:233-244.

Kok J (1996). Inducible gene expression and environmentally regulated genes in lactic acid bacteria. Antonie van Leeuwenhook 70:129-145.

Kuipers O P, de Ruyter P G, Kleerebezem M and de Vos W M (1997). Controlled overproduction of proteins by lactic acid bacteria. Trends Biotechnol. 15:135-140.

Langella P and Le Loir Y (1999). Heterologous protein secretion in *Lactococcus lactis*: a novel antigen delivery system. Braz. J. Med. Biol. Res. 32:191-198.

Le Loir Y, Gruss A, Ehrlich S D and Langella P (1994). Direct screening of recombinants in gram-positive bacteria using the secreted staphylococcal nuclease as a reporter. J. Bacteriol. 178:4333.

Le Loir Y, Gruss A, Ehrlich S D and Langella P (1998). A nine-residue synthetic propeptide enhances secretion efficiency of heterologous proteins in *Lactococcus lactis*. J. Bacteriol. 180:1895-1903.

Loubiere P, Cocaign-Bousquet M, Matos J, Goma G and Lindley N D (1997). Influence of end-products inhibition and nutrient limitations on the growth of *Lactococcus lactis* subsp. *lactis*. J. Appl. Microbiol. 82:95-100.

Madsen S M, Arnau J, Vrang A, Givskov M and Israelsen H (1999). Molecular characterization of the pH-inducible and growth phase-dependent promoter P170 of *Lactococcus lactis*. Mol. Microbiol. 32:75-87.

Martin, G: A. and Hempfling, W. P. (1976). A method for the regulation of microbial population density during continuous culture at high growth rates. Arch. Microbiol. 107:41-47.

Nauta A, van Sinderen D, Karsens H, Smit E, Venema G and Kok J (1997). Design of thermolabile bacteriophage repressor mutants by comparative molecular modeling. Nat. Biotechnol. 15:980-983.

O'Sullivan D J and Klaenhammer T R (1993a). High- and low-copy-number Lactoccus shuttle cloning vectors with features for clone screening. Gene 137:227-231.

O'Sullivan D J and Klaenhammer T R (1993b) Rapid Mini-Prep Isolation of High-Quality Plasmid DNA from Lactococcus and Lactobacillus spp. Appl. Environ. Microbiol. 59:2730-2733.

O'Sullivan D J, Walker S A, West S G and Klaenhammer T R (1996). Development of an expression strategy using a lytic phage to trigger explosive plasmid amplification and gene expression. Biotechnology (N.Y.) 14:82-87.

Poquet I, Ehrlich S D and Gruss A (1998). An export-specific reporter designed for gram-positive bacteria: application to *Lactococcus lactis*. J. Bacteriol. 180:1904-1912.

Ravn P, Arnau J, Madsen S M, Vrang A and Israelsen H (2000). The development of TnNuc and its use for the isolation of novel secretion signals in *Lactococcus lactis*. Gene 242:347-356.

Sambrook J, Fritsch E F and Maniatis T (1989). Molecular cloning: A Laboratory Manual. Cold Spring Harbor Laboratory.

Sanders J W, Venema G, Kok J and Leenhouts K (1998). Identification of a sodium chloride-regulated promoter in *Lactococcus lactis* by single-copy chromosomal fusion with a reporter gene. Mol. Gen. Genet. 257:681-685.

van Asseldonk M, Rutten G, Oteman, M, Siezen R J, de Vos W M and Simons G (1990). Gene 95:155-160.

van Asseldonk M, Simons A, Visser H, de Vos W M and Simons G (1993). Cloning, nucleotide sequence, and regulatory analysis of the *Lactococcus lactis* dnaJ gene. J. Bacteriol. 175:1637-1644.

van der Vossen J M, van der Lelie D and Venema G (1987). Isolation and characterization of *Streptococcus cremoris* Wg2-specific promoters. Appl. Environ. Microbiol. 53:2452-2457.

Walker S A and Klaenhammer T R (1998). Molecular characterization of a phage-inducible middle promoter and its transcriptional activator from the lactococcal bacteriophage phi31. J. Bacteriol. 180:921-931.

---

The invention claimed is:

1. A method of producing a heterologous peptide, polypeptide or protein in a *Lactococcus lactis* bacterium, the method comprising the steps of:
   (i) constructing a recombinant *Lactococcus lactis* bacterium comprising a nucleotide sequence coding for the heterologous peptide, polypeptide or protein and operably linked thereto, appropriate regulatory nucleotide sequences to control the expression of the coding sequence,
   (ii) cultivating said recombinant bacterium under fed-batch or continuous cultivation conditions in a chemically defined medium, to express the nucleotide sequence, and
   (iii) harvesting the recombinant bacterium or the peptide, polypeptide or protein, wherein the concentration of glucose is kept at a pre-selected concentration of at least about 0.5 g/L by controlled feeding of glucose.

2. A method according to claim 1 wherein the recombinant bacterium comprises a constitutive promoter operably linked to the coding sequence.

3. A method according to claim 1 wherein the recombinant bacterium comprises a regulatable promoter operably linked to the coding sequence.

4. A method according to claim 3 wherein the regulatable promoter is regulated by accumulation of a metabolite intracellularly or in the medium.

5. A method according to claim 3 wherein the regulatable promoter is obtained from a lactic acid bacterium.

6. A method according to claim 5 wherein the regulatable promoter is the P170 promoter.

7. A method according to claim 3 wherein the promoter is introduced into the recombinant bacterium on an autonomously replicating replicon.

8. A method according to claim 3 wherein the promoter is a promoter not naturally associated with the nucleotide sequence coding for the heterologous peptide, polypeptide or protein.

9. A method according to claim 1 wherein the heterologous peptide, polypeptide or protein is selected from the group consisting of an enzyme and a pharmaceutically active compound.

10. A method according to claim 1 wherein the coding nucleotide sequence is operably linked to a nucleotide sequence coding for a signal peptide (SP).

11. A method according to claim 10 wherein the signal peptide is selected from the group consisting of the usp45 signal peptide and the signal peptide having the sequence MKFNKKRVAIATFIALIFVSFFTISSQDAQAAERS (SEQ ID NO: 1).

12. A method according to claim 1 wherein the control of feeding of glucose to the medium is linked to pH control.

13. A method according to claim 1 wherein the yield of heterologous peptide, polypeptide or protein is at least 5 mg/L.

14. A method according to claim 1 wherein the chemically defined medium is the medium comprising:

| Component | Concentration, mM or +/− |
| --- | --- |
| L-Alanine | 3.4 |
| L-Arginine | 1.1 |
| L-Asparagine | 0.8 |
| L-Cysteine | 0.8 |
| L-Glutamate | 2.1 |
| L-Glutamine | 0.7 |
| Glycine | 2.7 |
| L-Histidine | 0.3 |
| L-Isoleucine | 0.8 |
| L-Leucine | 0.8 |
| L-Lysine-HCl | 1.4 |
| L-Methionine | 0.7 |
| L-Phenylalanine | 1.2 |
| L-Proline | 2.6 |
| L-Serine | 2.9 |
| L-Threonine | 1.7 |
| L-Tryptophan | 0.5 |
| L-Tyrosine | 0.3 |
| L-Valine | 0.9 |
| $K_2SO_4$ | 0.28[a] |
| $KH_2PO_4/K_2HPO_4$ | 4/6 |
| Na-acetate | 15 |
| $CaCl_2$ | 0.0005[a] |
| $MgCl_2$ | 0.52[a] |
| $FeSO_4$ | 0.01[a] |
| Vitamins[b] | + |
| Micronutrients[a,c] | + |
| Citric acid | 0.1 |

[a] From Neidhardt et al. J. Bacteriol. 119: 736-747;
[b] Vitamins: 0.4 μM biotin, 10 μM pyridoxal-HCl, 2.3 μM folic acid, 2.6 μM riboflavin, 8 μM niacinamide, 3 μM thiamine-HCl and 2 μM pantothenate;
[c] Micronutrients: 0.003 μM $(NH_4)_6(MO_7)_{24}$, 0.4 μM $H_3BO_4$, 0.03 μM $CoCl_2$, 0.01 μM $CuSO_4$, 0.08 μM $MnCl_2$ and 0.01 μM $ZnSO_4$, or wherein the components of said chemically defined medium are present in three-fold or five-fold amounts of the enumerated concentrations, except the phosphates and sodium acetate, the respective amounts of which are kept at the enumerated concentrations.

15. A method according to claim 1 wherein the chemically defined medium is the medium comprising:

| Component | Concentration, mM or +/− |
| --- | --- |
| L-Alanine | 3.4 |
| L-Arginine | 1.1 |
| L-Asparagine | 0.8 |
| L-Cysteine | 0.8 |
| L-Glutamate | 2.1 |
| L-Glutamine | 0.7 |
| Glycine | 2.7 |
| L-Histidine | 0.3 |
| L-Isoleucine | 0.8 |
| L-Leucine | 0.8 |
| L-Lysine-HCl | 1.4 |
| L-Methionine | 0.7 |
| L-Phenylalanine | 1.2 |
| L-Proline | 2.6 |

-continued

| Component | Concentration, mM or +/- |
|---|---|
| L-Serine | 2.9 |
| L-Threonine | 1.7 |
| L-Tryptophan | 0.5 |
| L-Tyrosine | 0.3 |
| L-Valine | 0.9 |
| $K_2SO_4$ | 0.28[a] |
| $KH_2PO_4/K_2HPO_4$ | 4/6 |
| Na-acetate | 15 |
| $CaCl_2$ | 0.0005[a] |
| $MgCl_2$ | 0.52[a] |
| $FeSO_4$ | 0.01[a] |
| Vitamins[b] | + |
| Micronutrients[a,c] | + |
| Citric acid | 0.1 |

[a]From Neidhardt et al. J. Bacteriol. 119:736-747;
[b]Vitamins: 0.4 μM biotin, 10 μM pyridoxal-HCl, 2.3 μM folic acid, 2.6 μM riboflavin, 8 μM niacinamide, 3 μM thiamine-HCl and 2 μM pantothenate;
[c]Micronutrients: 0.003 μM $(NH_4)_6(MO_7)_{24}$, 0.4 μM $H_3BO_4$, 0.03 μM $CoCl_2$, 0.01 μM $CuSO_4$, 0.08 μM $MnCl_2$ and 0.01 μM $ZnSO_4$;

wherein glucose is additionally included in the chemically defined medium in an amount in the range of 1-100 g/L, or wherein glucose is additionally included in the chemically defined medium in an amount in the range of 1-100 g/L and wherein the components of said chemically defined medium are present in three-fold or five-fold amounts of the enumerated concentrations, except the phosphates and sodium acetate, the respective amounts of which are kept at the enumerated concentrations.

16. A method of producing a heterologous peptide, polypeptide or protein in a *Lactococcus lactis*, the method comprising the steps of
(i) constructing a recombinant *Lactococcus lactis* bacterium comprising a nucleotide sequence coding for the heterologous peptide, polypeptide or protein and operably linked thereto, appropriate regulatory nucleotide sequences to control the expression of the coding sequence,
(ii) cultivating said recombinant bacterium under fed-batch or continuous cultivation conditions in a chemically defined medium supplemented with yeast extract, to express the nucleotide sequence, and
(iii) harvesting the recombinant bacterium or the peptide, polypeptide or protein,
wherein the concentration of glucose is kept at a preselected concentration of at least about 0.5 g/L by controlled feeding of glucose.

17. A method according to claim 16 wherein the recombinant bacterium comprises a constitutive promoter operably linked to the coding sequence.

18. A method according to claim 16 wherein the recombinant bacterium comprises a regulatable promoter operably linked to the coding sequence.

19. A method according to claim 18 wherein the regulatable promoter is regulated by accumulation of a metabolite intracellularly or in the medium.

20. A method according to claim 18 wherein the regulatable promoter is obtained from a lactic acid bacterium.

21. A method according to claim 20 wherein the promoter is the P170 promoter.

22. A method according to claim 18 wherein the promoter is introduced into the recombinant bacterium on an autonomously replicating replicon.

23. A method according to claim 18 wherein the promoter is a promoter not naturally associated with the nucleotide sequence coding for the heterologous peptide, polypeptide or protein.

24. A method according to claim 16 wherein the heterologous peptide, polypeptide or protein is selected from the group consisting of an enzyme and a pharmaceutically active compound.

25. A method according to claim 16 wherein the coding nucleotide sequence is operably linked to a nucleotide sequence coding for a signal peptide (SP).

26. A method according to claim 25 wherein the signal peptide is selected from the group consisting of the Usp45 signal peptide and the signal peptide having the sequence MKFNKKRVAIATFIALIFVSFFTISSQDAQAAERS (SEQ ID NO: 1).

27. A method according to claim 16 wherein the control of feeding of glucose to the medium is linked to pH control.

28. A method according to claim 16 wherein the amount of yeast extract is in the range of 0.1-10 g/L.

29. A method according to claim 16 wherein the yield of heterologous peptide, polypeptide or protein is at least 5 mg/L.

30. A method according to claim 16 wherein the chemically defined medium is the medium comprising:

| Component | Concentration, mM or +/- |
|---|---|
| L-Alanine | 3.4 |
| L-Arginine | 1.1 |
| L-Asparagine | 0.8 |
| L-Cysteine | 0.8 |
| L-Glutamate | 2.1 |
| L-Glutamine | 0.7 |
| Glycine | 2.7 |
| L-Histidine | 0.3 |
| L-Isoleucine | 0.8 |
| L-Leucine | 0.8 |
| L-Lysine-HCl | 1.4 |
| L-Methionine | 0.7 |
| L-Phenylalanine | 1.2 |
| L-Proline | 2.6 |
| L-Serine | 2.9 |
| L-Threonine | 1.7 |
| L-Tryptophan | 0.5 |
| L-Tyrosine | 0.3 |
| L-Valine | 0.9 |
| $K_2SO_4$ | 0.28[a] |
| $KH_2PO_4/K_2HPO_4$ | 4/6 |
| Na-acetate | 15 |
| $CaCl_2$ | 0.0005[a] |
| $MgCl_2$ | 0.52[a] |
| $FeSO_4$ | 0.01[a] |
| Vitamins[b] | + |
| Micronutrients[a,c] | + |
| Citric acid | 0.1 |

[a]From Neidhardt et al. J. Bacteriol. 119:736-747;
[b]Vitamins: 0.4 μM biotin, 10 μM pyridoxal-HCl, 2.3 μM folic acid, 2.6 μM riboflavin, 8 μM niacinamide, 3 μM thiamine-HCl and 2 μM pantothenate;
[c]Micronutrients: 0.003 μM $(NH_4)_6(MO_7)_{24}$, 0.4 μM $H_3BO_4$, 0.03 μM $CoCl_2$, 0.01 μM $CuSO_4$, 0.08 μM $MnCl_2$ and 0.01 μM $ZnSO_4$;

wherein the components of said chemically defined medium are present in three-fold or five-fold amounts of the enumerated concentrations, except the phosphates and sodium acetate, the respective amounts of which are kept at the enumerated concentrations.

31. A method according to claim 16 wherein the chemically defined medium is the medium comprising:

| Component | Concentration, mM or +/− |
|---|---|
| L-Alanine | 3.4 |
| L-Arginine | 1.1 |
| L-Asparagine | 0.8 |
| L-Cysteine | 0.8 |
| L-Glutamate | 2.1 |
| L-Glutamine | 0.7 |
| Glycine | 2.7 |
| L-Histidine | 0.3 |
| L-Isoleucine | 0.8 |
| L-Leucine | 0.8 |
| L-Lysine-HCl | 1.4 |
| L-Methionine | 0.7 |
| L-Phenylalanine | 1.2 |
| L-Proline | 2.6 |
| L-Serine | 2.9 |
| L-Threonine | 1.7 |
| L-Tryptophan | 0.5 |
| L-Tyrosine | 0.3 |
| L-Valine | 0.9 |
| $K_2SO_4$ | 0.28[a] |
| $KH_2PO_4/K_2HPO_4$ | 4/6 |
| Na-acetate | 15 |
| $CaCl_2$ | 0.0005[a] |
| $MgCl_2$ | 0.52[a] |
| $FeSO_4$ | 0.01[a] |
| Vitamins[b] | + |
| Micronutrients[a,c] | + |
| Citric acid | 0.1 |

[a] From Neidhardt et al. J. Bacteriol. 119:736-747;
[b] Vitamins: 0.4 μM biotin, 10 μM pyridoxal-HCl, 2.3 μM folic acid, 2.6 μM riboflavin, 8 μM niacinamide, 3 μM thiamine-HCl and 2 μM pantothenate;
[c] Micronutrients: 0.003 μM $(NH_4)_6(MO_7)_{24}$, 0.4 μM $H_3BO_4$, 0.03 μM $CoCl_2$, 0.01 μM $CuSO_4$, 0.08 μM $MnCl_2$ and 0.01 μM $ZnSO_4$;

wherein glucose is additionally included in the chemically defined medium in an amount in the range of 1-100 g/L, or wherein glucose is additionally included in the chemically defined medium in an amount in the range of 1-100 g/L and wherein the components of said chemically defined medium are present in three-fold or five-fold amounts of the enumerated concentrations, except the phosphates and sodium acetate, the respective amounts of which are kept at the enumerated concentrations.

* * * * *

SEQUENCE LISTING

```
<160> NUMBER OF SEQ ID NOS: 9

<210> SEQ ID NO 1
<211> LENGTH: 35
<212> TYPE: PRT
<213> ORGANISM: Artificial Sequence
<220> FEATURE:
<223> OTHER INFORMATION: SP310mut2

<400> SEQUENCE: 1

Met Lys Phe Asn Lys Lys Arg Val Ala Ile Ala Thr Phe Ile Ala Leu
1               5                   10                  15

Ile Phe Val Ser Phe Phe Thr Ile Ser Ser Gln Asp Ala Gln Ala Ala
            20                  25                  30

Glu Arg Ser
        35

<210> SEQ ID NO 2
<211> LENGTH: 72
<212> TYPE: DNA
<213> ORGANISM: Artificial Sequence
<220> FEATURE:
<223> OTHER INFORMATION: Usp Primer 1

<400> SEQUENCE: 2
tagtaggatc ccgggtctag attagggtaa ctttgaaagg atattcctca tgaaaaaaaa      60
gattatctca gc                                                          72
```

<210> SEQ ID NO 3
<211> LENGTH: 40
<212> TYPE: DNA
<213> ORGANISM: Artificial Sequence
<220> FEATURE:
<223> OTHER INFORMATION: Usp Primer 2

<400> SEQUENCE: 3
acgcgtcgac ctgcagagat cttgtgtcag cgtaaacacc                40

<210> SEQ ID NO 4
<211> LENGTH: 27
<212> TYPE: DNA
<213> ORGANISM: Artificial Sequence
<220> FEATURE:
<223> OTHER INFORMATION: Ter 1 primer

<400> SEQUENCE: 4
tagtagtcga caaccgggtg ttgggag                              27

<210> SEQ ID NO 5
<211> LENGTH: 27
<212> TYPE: DNA
<213> ORGANISM: Artificial Sequence
<220> FEATURE:
<223> OTHER INFORMATION: rrncTT Xho I Primer

<400> SEQUENCE: 5
ggccgctcga gggcgcaaaa tagcgat                              27

<210> SEQ ID NO 6
<211> LENGTH: 21
<212> TYPE: DNA
<213> ORGANISM: Artificial Sequence
<220> FEATURE:
<223> OTHER INFORMATION: pAK80rev2 Primer

<400> SEQUENCE: 6
cccatttagc cgtcatttca g                                    21

<210> SEQ ID NO 7
<211> LENGTH: 57
<212> TYPE: DNA
<213> ORGANISM: Artificial Sequence
<220> FEATURE:
<223> OTHER INFORMATION: LBEp041 Primer

<400> SEQUENCE: 7
gtcgacctgc agactagtga tatcagatct agccatgggg aatatccttt caaagtt    57

<210> SEQ ID NO 8
<211> LENGTH: 27
<212> TYPE: DNA
<213> ORGANISM: Artificial Sequence
<220> FEATURE:
<223> OTHER INFORMATION: Nuc1 Primer

<400> SEQUENCE: 8
ggaagatctt cacaaacaga taacggc                              27

<210> SEQ ID NO 9
<211> LENGTH: 39
<212> TYPE: DNA
<213> ORGANISM: Artificial Sequence
<220> FEATURE:
<223> OTHER INFORMATION: Nuc2 Primer

```
<400> SEQUENCE: 9
acgcgtcgac gaattcgatc taaaaattat aaaagtgcc                                39
```